(12) United States Patent
Bogenstaetter et al.

(10) Patent No.: US 6,638,967 B2
(45) Date of Patent: Oct. 28, 2003

(54) THIOPHENE OF FURAN PYRROLIDINE COMPOUNDS

(75) Inventors: Michael Bogenstaetter, Del Mar, CA (US); Wenying Chai, San Diego, CA (US); Annette K. Kwok, San Diego, CA (US)

(73) Assignee: Ortho-McNeil Phamraceutical, Inc., Raritan, NJ (US)

( * ) Notice: Subject to any disclaimer, the term of this patent is extended or adjusted under 35 U.S.C. 154(b) by 0 days.

(21) Appl. No.: 09/922,622

(22) Filed: Aug. 6, 2001

(65) Prior Publication Data

US 2002/0037896 A1 Mar. 28, 2002

Related U.S. Application Data

(60) Provisional application No. 60/223,768, filed on Aug. 8, 2000.

(51) Int. Cl.[7] ............... A61K 31/341; A61K 31/381; C07D 409/14; C07D 407/14
(52) U.S. Cl. ............... 514/422; 514/231.5; 514/258; 514/326; 548/527; 548/517; 546/187; 546/212; 546/268.1; 546/269.7; 546/281.7; 544/106; 544/147; 544/152
(58) Field of Search ............... 548/527, 517, 548/561, 465, 563, 564, 146, 453, 452; 546/187, 207, 212, 268.1, 269.7, 280.1, 281.7; 544/106, 147, 152; 514/231.5, 258.13, 254.1, 326, 365, 385, 406, 408–422

(56) References Cited

U.S. PATENT DOCUMENTS

| 3,919,231 | A | * | 11/1975 | Pelosi et al. ............... 544/333 |
| 5,217,986 | A | | 6/1993 | Pomponi et al. |
| 5,352,707 | A | | 10/1994 | Pompni et al. |
| 5,840,746 | A | * | 11/1998 | Ducharme et al. .......... 514/365 |
| 5,869,479 | A | | 2/1999 | Kreutner et al. |
| 5,929,089 | A | | 7/1999 | Jegham et al. |

FOREIGN PATENT DOCUMENTS

| EP | 0 978 512 A1 | 2/2000 |
| EP | 0 982 300 A3 | 3/2000 |
| EP | 0 982 300 A2 | 3/2000 |
| WO | WO 93 20061 A | 11/1993 |
| WO | 9504052 | * 2/1995 |
| WO | WO 95 14007 A | 5/1995 |
| WO | WO 97 17345 A | 5/1997 |
| WO | WO 99/42458 A1 | 8/1999 |
| WO | WO 00/06254 A2 | 2/2000 |

OTHER PUBLICATIONS

Caplus English Abstract WO 2001032633 Guerry et al 2001.*
Holger Stark et al.: *Developments of histamine H3–antagonists*, Drugs Of The Future, 1996, pp. 507–520, vol. 21, No. 5, XP002084872 Barcelona, ES ISSN: 0377–8282.
Ronald Wolin et al.: *Novel H3 Receptor Antagonists. Sulfonamide Homologs of Histamine*; Bioorganic & Medicinal Chemistry Letters, 1998, pp. 2157–2162, No. 8; XP004137238 Oxford, GB ISSN: 0960–894X.
PCT International Search Report PCT/US01/24654 dated Apr. 18, 2002.
Ganellin, C.R. et al.; "Synthesis of Potent Non–imidazole Histamine H3–Receptor Antagonists"; Arch. Pharm. Pharm. Med.Chem. (Weinheim, Ger.); 1998 331:395–404.
Meier, G. et al.; "Influence of imidazole replacement in different structural classes of histamine H3–receptor antagonists"; Eur. J. Pharm. Sci.; 2001; 13:249–259.
Albengres, E. et al.; "Systemic Antifungal Agents"; Drug Safety; Feb. 1998; 18(2):83–97.
Ali, S.M. et al., "Design, Synthesis, and Structure–Activity Relationships of Acetylene–Based Histamine H3 Receptor Antagonists"; J. Med. Chem.; 1999 42:903–909.
Arrang, J.M. et al.; "Auto–inhibition of brain histamine release mediated by a novel class (h3) of histamine receptor" Nature; Apr. 1983; 302:832–837.
Ash, A.S.F. et al; "Receptors Mediating Some Actions of Histamine"; Br. J. Pharmac. Chemother.; 1966 27:427–439.
Back, D.J.; et al; "Inhibition of tolbutamide metabolism by substituted imidazole drugs in vivo:evidence for a structure–activity relationship"; Br. J. Pharmacol.; 1985 85:121–126.
Barnes, J.C. et al; "The selective Histamine H3 Receptor Antagonist Thioperamide Improves Cognition and Enhances Hippocampal Acetylcholine Release in vivo"; Soc. Neurosci. Abstr.; 1993 19:1813.
Black, J.W. et al.; "Definition and Antagonism of Histamine H2–receptors"; Nature; Apr. 1972; 236:385–390.
Garbag, M. et al; "S–[2–(4–Imidazolyl)ethyl]Isothiourea, a Highly Specific and Potent Histamine H3 Receptor Agonist"; J. Pharmacol. Exp. Ther.; 1992; 263(1):304–310.
Gilatech, Inc.; "Other News To Note"; Bioworld Today, Mar. 2, 1999, p. 3.
Gilatech, Inc.; "Gilatech's first drug candidate begins phase I human clinical trials"; Gilatech Inc. Press Release; Nov. 5, 1998.

(List continued on next page.)

*Primary Examiner*—Rita Desai

(57) ABSTRACT

Compounds of Formula I

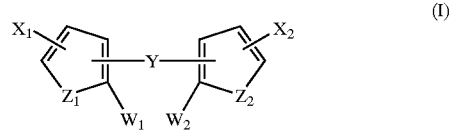

Wherein Z2 is an Oxygen or a Sulfur, Z1 is —CH═CH— and Y is a bond, W1 and W2 are hydrogens and X1 and X2 are various heterocyclic rings are disclosed.

7 Claims, No Drawings

OTHER PUBLICATIONS

Ichinose, M. et al; "Histamine H3–receptors modulate nonadrenergic noncholinergic neural bronchoconstriction in guinea–pig in vivo"; P.J. Eur. J. Pharmacol; 1989; 174:49–55.

Imamura, M. et al.; "Unmasking of Activated Histamine H3–Receptors in Myocardial Ischemia: Their Role as Regulators of Exocytotic Norepinephrine Release 1,2"; J. Pharmacol, Exp. Ther.; 1994; 271(3):1259–1266.

Kapetanovic, I.M. et al; "Nafimidone, An Imidazole Anticonvulsant, and its Metabolite as Potent Inhibitors of Microsomal Metabolism of Phenytoin and Carbamazepine"; H. J. Drug Metab. Dispos.; 1984 12(5):560–564.

Korte, A. et al; "Characterization and Tissue Distribution of H3 Histamine Receptors in Guinea Pigs by Na–Methylhistamine"; Biochem. Biophys. Res. Commun.; May 1990; 168(3):979–986.

Krause, M. et al.; "The Histamine H3 Receptor–A Target for New Drugs"; Leurs, R.; Timmerman, H. (Eds.); Elsevier; 1998;175–196.

Phillips, J. G. et al; ";The Histamine H3 Receptor–A Target for New Drugs"; Leurs, R.; Timmerman, H. (Eds.); Elsevier; 1998; 197–222.

Lavrijsen, K. et al; "Induction Potential of Antifungals Containing an Imidazole or Triazole Moiety"; Biochem. Pharmacol.; 1986 35(11):1867–1878.

Leurs, R. et al; "The medicinal chemistry and therapeutic potentials of ligands of the histamine h3 receptor" Prog. Drug. Res.; 1995; 45:107–165.

Lin, Jian–Sheng et al. "Involvement of histaminergic neurons in arousal mechanisms demonstrated with H3–receptor ligands in the cat"; Brain Res.; 1990; 523:325–330.

Linney, I.D. et al; "Design, Synthesis, and Structure–Activity Relationships of Novel Non–Imidazole Histamine H3 Receptor Antagonists"; J. Med. Chem.; 2000; 43:2362–2370.

Lovenberg, T.W. et al; "Cloning and Functional Expression of the Human Histamine H3 Receptor"; Mol. Pharmacol; 1999 55:1101–1107.

Machidori, H. et al; "Zucker obese rats:defect in brain histamine control of feeding"; Brain Res.; 1992; 590:180–186.

McLeod, R.L. et al; "Antimigraine and Sedative Activity of SCH 50971: A Novel Orally–Active Histamine H3 Receptor Agonist"; Soc. Neurosci. Abstr.; 1996; 22:2010.

Monti, J.M. et al; "Effects of selective activation or blockade of the histamine h3 receptor on sleep and wakefulness"; Eur. J. Pharmacol.; 1991; 205:283–287.

Morisset, S. et al; "High constitutive activity of native H3 receptors regulates histamine neurons in brain"; Nature; Dec., 2000; 408:860–864.

Oda, Tamaki et al.; "Molecular Cloning and characterization of a Novel Type of Histamine Receptor Preferentially Expressed in Leukocytes"; J. Biol. Chem.; Nov. 2000; 275(47):36781–36786.

Panula, P. et al.; "Significant Changes in the Human Brain Histaminergic System in Alzheimer's Disease"Soc. Neurosci. Abstr.; 1995; 21:1977.

Rouleau, A. et al.; "Bioavailability, Antinociceptive and Antiinflammatory Properties of BP 2–94, a Histamine H3 Receptor Agonist Prodrug"; J. Pharmacol. Exp. Ther.; 1997 281(3):1085–1094.

Schlicker, E., et al.; "The moderate affinity of clozapine at H3 receptors is not shared by its two major metab olites and by structurally related and unrelated atypical neuroleptics"; Naunyn–Schmiedeberg's Arch. Pharmacol.; 1996 353:290–294.

Sheets, Joel J., et al.; "Ketoconazole: A Potent Inhibitor of Cytochrome P–450–Dependent Drug Metabolism in Rat Liver", Drug Metab. Dispos.; 1984; 12(5):603–606.

Stark, H. et al.; "Developments of histamine H3–receptor antagonists"; Drugs Future; 1996; 21(5):507–520.

Tozer, M.J., et al.: "Histamine H3 receptor antagonists"; Exp. Opin. Ther. Patents; 2000 10:1045–1055.

Walczynski, K. , et al.; "Non–Imidazole Histamine H3 Ligands, Part 2: New 2–Substituted Benzothiazoles as Histamine H3 Antagonists"; Arch. Pharm. Pharm. Med. Chem. (Weinheim, Ger.); 1999 332:389–398.

Walczynski, K. et al.; "Non–imidazole histamine H3 ligands. Part I. Synthesis of 2–(1–piperazinyl)–and 2–hexahydro–1 H–1,4–diazepin–1–yl)benzoyhiazole derivatives as H3 antagonists with H1 blocking activities"; IL Farmaco; 1999; 54:684–694.

West, R.E. Jr. et al.; "The Profiles of Human and Primate [3H]Na–Methylhistamine Binding Differ From That of Rodents"; Eur. J. Pharmacol.; 1999; 377:233–239.

Yokohama, H. et al., "Effect of thioperamide, a histamine h3 receptor antagonists, on electrically induced convulsions in mice"; Eur. J. Pharmacol. ; 119 234:129–133 1993.

* cited by examiner

US 6,638,967 B2

THIOPHENE OF FURAN PYRROLIDINE COMPOUNDS

RELATED APPLICATION

This application is related to U.S. Ser. No. 60/223,768, a provisional application filed on Aug. 8, 2000, now abandoned.

FIELD OF THE INVENTION

The present invention relates to bicyclic derivatives, their synthesis and their use, for example, for the treatment of disorders and conditions mediated by the histamine receptor.

BACKGROUND OF THE INVENTION

Histamine [2-(imidazol-4-yl)ethylamine] is a transmitter substance. Histamine exerts a physiological effect via multiple distinct G-protein coupled receptors. It plays a role in immediate hypersensitivity reactions and is released from mast cells following antigen IgE antibody interaction. The actions of released histamine on the vasculature and smooth muscle system account for the symptoms of the allergic response. These actions occur at the $H_1$ receptor (Ash, A. S. F. and Schild, H. O., *Br. J. Pharmacol.,* 1966, 27, 427) and are blocked by the classical antihistamines (e.g. diphenhydramine). Histamine is also an important regulator of gastric acid secretion through its action on parietal cells. These effects of histamine are mediated via the $H_2$ receptor (Black, J. W., Duncan, W. A. M., Durant, C. J., Ganellin, C. R. and Parsons, E. M., *Nature,* 1972, 236, 385) and are blocked by $H_2$ receptor antagonists (e.g. cimetidine). The third histamine receptor—$H_3$—was first described as a presynaptic autoreceptor in the central nervous system (CNS) (Arrang, J.-M., Garbarg, M., and Schwartz, J.-C., *Nature* 1983, 302, 832) controlling the synthesis and release of histamine. Recent evidence has emerged showing that the $H_3$ receptors are also located presynaptically as heteroreceptors on serotonergic, noradrenergic, dopaminergic, cholinergic, and GABAergic (gamma-aminobutyric acid containing) neurons. These $H_3$ receptors have also recently been identified in peripheral tissues such as vascular smooth muscle. Consequently there are many potential therapeutic applications for histamine $H_3$ agonists, antagonists, and inverse agonists. (See: "*The Histamine $H_3$ Receptor-A Target for New Drugs*", Leurs, R., and Timmerman, H., (Editors), Elsevier, 1998; Morisset et al., *Nature,* 2000, 408, 860-864.) A fourth histamine receptor—$H_4$—was recently described by Oda et al., (J. Biol. Chem., 2000, 275, 36781-36786).

The potential use of histamine $H_3$ agonists in sleep/wake and arousal/vigilance disorders is suggested based on animal studies (Lin et al, *Br. Res.,* 1990, 523, 325; Monti et al *Eur. J. Pharmacol.,* 1991, 205, 283). Their use in the treatment of migraine has also been suggested (McLeod et al *Abstr. Society Neuroscience,* 1996, 22, 2010) based on their ability to inhibit neurogenic inflammation. Other applications could be a protective role in myocardial ischemia and hypertension where blockade of norepinephrine release is beneficial (Imamura et al *J. Pharmacol. Expt. Ther.,* 1994, 271,1259). It has been suggested that histamine $H_3$ agonists may be beneficial in asthma due to their ability to reduce non-adrenergic non-cholinergic (NANC) neurotransmission in airways and to reduce microvascular leakage (Ichinose et al *Eur. J. Pharmacol.,* 1989,174, 49).

Several indications for histamine $H_3$ antagonists and inverse agonists have similarly been proposed based on animal pharmacology experiments with known histamine $H_3$ antagonists (e.g. thioperamide). These include dementia, Alzheimer's disease (Panula et al *Abstr. Society Neuroscience,* 1995, 21,1977), epilepsy (Yokoyama et al *Eur. J. Pharmacol.,* 1993, 234,129) narcolepsy, eating disorders (Machidori et al *Brain Research* 1992, 590,180), motion sickness, vertigo, attention deficit hyperactivity disorders (ADHD), learning and memory (Barnes et al *Abstr. Society Neuroscience,* 1993,19,1813), schizophrenia (Schlicker et al *Naunyn-Schmiedeberg's Arch. Pharmacol.,* 1996, 353, 290-294); (also see; Stark et al *Drugs Future,* 1996, 21, 507 and Leurs et al *Progress in Drug Research,* 1995, 45, 107 and references cited therein). Histamine $H_3$ antagonists, alone or in combination with a histamine $H_1$ antagonist, are reported to be useful for the treatment of upper airway allergic response (U.S. Pat. Nos. 5,217,986; 5,352,707 and 5,869,479). Recently, a histamine $H_3$ antagonist (GT-2331) was identified and is being developed by Gliatech Inc. (Gliatech Inc. Press Release Nov. 5,1998; *Bioworld Today,* Mar. 2,1999) for the treatment of CNS disorders.

As noted, the prior art related to histamine $H_3$ ligands has been comprehensively reviewed ("*The Histamine $H_3$ Receptor-A Target for New Drugs*", Leurs, R., and Timmerman, H., (Editors), Elsevier, 1998). Within this reference the medicinal chemistry of histamine $H_3$ agonists and antagonists was reviewed (see Krause et al and Phillips et al respectively). The importance of an imidazole moiety containing only a single substitution in the 4 position was noted together with the deleterious effects of additional substitution on activity. Particularly methylation of the imidazole ring at any of the remaining unsubstituted positions was reported to strongly decrease activity. Additional publications support the hypothesis that an imidazole function is essential for high affinity histamine $H_3$ receptor ligands (See, Ali et al *J. Med. Chem.,* 1999, 42, 903 and Stark et al, *Drugs Future,* 1996, 21, 507 and references cited therein). However many imidazole containing compounds are substrates for histamine methyl transferase, the major histamine metabolizing enzyme in humans, which leads to shortened half lives and lower bioavailability (See, Rouleau et al *J. Pharmacol. Exp. Ther.* 1997, 281,1085). In addition, imidazole containing drugs, via their interaction with the cytochrome P450 monooxygenase system, can result in unfavorable biotransformations due to enzyme induction or enzyme inhibition. (Kapetanovic et al *Drug Metab. Dispos.* 1984,12, 560; Sheets et al *Drug Metab. Dispos.* 1984,12, 603; Back, et al *Br. J. Pharmacol.* 1985, 85,121; Lavrijsen et al *Biochem. Pharmacol.* 1986, 35, 1867; *Drug Saf.,* 1998, 18, 83). The poor blood brain barrier penetration of earlier histamine $H_3$ receptor ligands may also be associated with the imidazole fragment (Ganellin et al *Arch. Pharm.* (*Weinheim,Ger.*) 1998, 331, 395).

More recently, several publications have described histamine $H_3$ ligands that do not contain an imidazole moiety. For example; Ganellin et al *Arch. Pharm.* (*Weinheim,Ger.*) 1998, 331, 395; Walczynski et al *Arch. Pharm.* (*Weinheim,Ger.*) 1999,332, 389; Walczynski et al Farmaco 1999, 684; Linney et al *J. Med. Chem.* 2000, 2362; Tozer and Kalindjian *Exp. Opin. Ther. Patents* 2000,10,1045-1055; U.S. Pat. No. 5,352,707; PCT Application W099/42458, Aug. 26,1999; and European Patent Application 0978512, Feb. 9, 2000.

The compounds of the present invention do not contain the imidazole moiety, and its inherent liabilities, and maintain potency at the human $H_3$ receptor. Thus in the present invention receptor binding was determined using the human histamine $H_3$ receptor (See Lovenberg et al *Mol. Pharmacol.*

1999, 1107). Screening using the human receptor is particularly important for the identification of new therapies for the treatment of human disease. Conventional binding assays for example are determined using rat synaptosomes (Garbarg et al *J. Pharmacol. Exp. Ther.* 1992, 263, 304), rat cortical membranes (West et al *Mol. Pharmacol.* 1990, 610), and guinea pig brain (Korte et al Biochem. *Biophys. Res. Commun.* 1990, 978). Only limited studies have been performed previously using human tissue but these allude to significant differences in the pharmacology of rodent and primate receptors (West et al *Eur. J. Pharmacol.* 1999, 233).

We now describe a series of bicyclic derivatives with the ability to modulate the activity of the histamine receptor, specifically the $H_3$ receptor, without the inherent problems associated with the presence of an imidazolyl moiety.

SUMMARY OF THE INVENTION

The present invention is directed to a compound of formula (I):

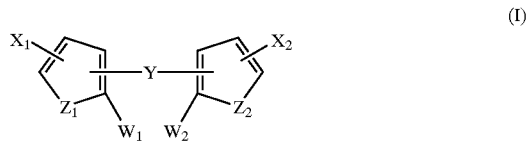

wherein each of $W_1$ and $W_2$ is H;

$X_1$ is selected from $G_a$, $R_a G_a$, $L_a G_a$, and $R_a L_a G_a$;

$X_2$ is selected from $G_b$, $R_b G_b$, $L_b G_b$, and $R_b L_b G_b$;

each of $G_a$ and $G_b$ is independently $NR_{3a}R_{4a}$ or $NR_{3b}R_{4b}$, respectively, or pyrrolidinyl, imidazolidinyl, pyrazolidinyl, piperidyl, isoindolinyl, morpholinyl, piperazinyl, imidazolyl, thiazolinyl, 5,6-dihydro-3-imidazo[2,1-B] thiazolyl, or thiazolyl; wherein each of $R_{3a}$, $R_{4a}$, $R_{3b}$ and $R_{4b}$ is independently selected from H, $C_{1-8}$ alkyl, $C_{3-7}$ cycloalkyl, and ($C_{3-7}$ cycloalkyl)$C_{1-6}$ alkyl;

$G_b$ can be further selected from nitro, halo, OH, CHO, pyrrolyl, or –C(=NOH)H;

each of $R_a$ and $R_b$ is independently O, S, NH or C=O;

each of $L_a$ and $L_b$ is independently $C_{1-3}$ alkylene;

Y is a covalent bond where one of $Z_1$ and $Z_2$ is N, O, or S; Y can also be $SO_2$, C=O, $CH_2$, $CH_2CH_2$, $OCH_2$, $CH_2O$, or $NR_C$, wherein $R_c$ is H, $C_{1-8}$ alkyl, $C_{3-7}$ cycloalkyl, ($C_{3-7}$ cycloalkyl)$C_{1-6}$ alkyl, $C_{2-5}$ heterocyclyl, ($C_{2-7}$ heterocyclyl) $C_{1-6}$ alkyl, phenyl, (phenyl)$C_{1-6}$ alkyl, or [di ($C_{1-6}$ alkyl) amino]$C_{1-6}$ alkyl;

each of $Z_1$ and $Z_2$ is independently N, O, S, or —CH=CH— to form a phenyl ring;

or a pharmaceutically acceptable salt, amide or ester thereof.

The invention also features a pharmaceutical composition comprising a compound of the invention and a pharmaceutically acceptable carrier; and methods of preparing or formulating such compositions. A composition of the invention may further include more than one compound of the invention, or a combination therapy (combination formulation or administering a combination of differently formulated active agents).

The invention also provides methods of treating certain conditions and diseases, each of which methods includes administering a therapeutically effective (or jointly effective) amount of a compound or composition of the invention to a subject in need of such treatment. The disclosed compounds are useful in methods for treating or preventing neurologic disorders including sleep/wake and arousal/vigilance disorders (e.g. insomnia and jet lag), attention deficit hyperactivity disorders (ADHD), learning and memory disorders, cognitive dysfunction, migraine, neurogenic inflammation, dementia, mild cognitive impairment (pre-dementia), Alzheimer's disease, epilepsy, narcolepsy, eating disorders, obesity, motion sickness, vertigo, schizophrenia, substance abuse, bipolar disorders, manic disorders and depression, as well as other histamine $H_3$ receptor mediated disorders such as upper airway allergic response, asthma, itch, nasal congestion and allergic rhinitis in a subject in need thereof. For example, the invention features methods for preventing, inhibiting the progression of, or treating upper airway allergic response, asthma, itch, nasal congestion and allergic rhinitis.

In yet another embodiment, the disclosed compounds may be used in a combination therapy method including administering a jointly effective dose of an $H_3$ antagonist and administering a jointly effective dose of a histamine $H_1$ antagonist, such as loratidine (CLARITIN™), desloratidine (CLARINEX™), fexofenadine (ALLEGRA™) and cetirizine (ZYRTEC™), for the treatment of allergic rhinitis, nasal congestion, and allergic congestion.

In yet another embodiment, the disclosed compounds may be used in a combination therapy method, including administering a jointly effective dose of an $H_3$ antagonist and administering a jointly effective dose of a neurotransmitter re-uptake blocker, such as a selective serotonin re-uptake inhibitor (SSRI) or a non-selective serotonin, dopamine or norepinephrine re-uptake inhibitor, including fluoxetine (PROZAC™), sertraline (ZOLOFT™), paroxetine (PAXIL™) and amitryptyline, for the treatment of depression, mood disorders or schizophrenia.

Additional features and advantages of the invention will become apparent from the detailed description and examples below, and the appended claims.

DETAILED DESCRIPTION OF THE INVENTION

The present invention provides bicyclic compounds useful for the treatment of disorders and conditions modulated by a histamine receptor.

A. Terms

Certain terms are defined below and by their usage throughout this disclosure.

As used herein, "halogen" shall mean chlorine, bromine, fluorine and iodine, or monovalent radicals thereof.

As used herein, the term "alkyl", whether used alone or as part of a substituent group, shall include straight and branched carbon chains. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1-4 carbon atoms. "Alkylene" refers to a bivalent hydrocarbyl group, such as methylene ($CH_2$), ethylene (—$CH_2$—$CH_2$—) or propylene (—$CH_2CH_2CH_2$—).

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, unless otherwise noted, "cycloalkyl" shall denote a three- to eight-membered, saturated monocyclic carbocyclic ring structure. Suitable examples include cyclopropyl, cyclobutyl, cyclopentyl, cyclohexyl, cycloheptyl and cyclooctyl.

As used herein, unless otherwise noted, "cycloalkenyl" shall denote a three- to eight-membered, partially unsaturated, monocyclic, carbocyclic ring structure, wherein the ring structure contains at least one double bond. Suitable examples include cyclohexenyl, cyclopentenyl, cycloheptenyl, cyclooctenyl, cyclohex-1,3-dienyl and the like.

As used herein, unless otherwise noted, "aryl" shall refer to carbocyclic aromatic groups such as phenyl, naphthyl, and the like. Divalent radicals include phenylene (-$C_6H_4$-) which is preferably phen-1,4-diyl, but may also be phen-1, 3-diyl.

As used herein, unless otherwise noted, "aralkyl" shall mean any alkyl group substituted with an aryl group such as phenyl, naphthyl and the like. Examples of aralkyls include benzyl, phenethyl, and phenylpropyl.

As used herein, unless otherwise noted, the terms "heterocycle", "heterocyclyl" and "heterocyclo" shall denote any five-, six-, or seven-membered monocyclic, nine or ten membered bicyclic or thirteen or fourteen membered tricyclic ring structure containing at least one heteroatom moiety selected from the group consisting of N, O, SO, $SO_2$, (C=O), and S, and preferably N, O, or S, optionally containing one to four additional heteroatoms in each ring. In some embodiments, the heterocyclyl contains between 1 and 3 or between 1 and 2 additional heteroatoms. Unless otherwise specified, a heterocyclyl may be saturated, partially unsaturated, aromatic or partially aromatic. The heterocyclyl group may be attached at any heteroatom or carbon atom which results in the creation of a stable structure.

Exemplary monocyclic heterocyclic groups can include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazaolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, hexahydroazepinyl, 4-piperidinyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dixolane and tetrahydro-1,1-dioxothienyl, dioxanyl, isothiazolidinyl, thietanyl, thiiranyl, triazinyl, triazolyl, tetrazolyl, azetidinyl and the like.

Exemplary bicyclic heterocyclic groups include benzthiazolyl, benzoxazolyl, benzoxazinyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopridyl, furopyridinyl (such as furo[2,3-c]pyridinyl, furo[3,1-b]pyridinyl), or furo[2,3-b]pyridinyl), dihydroisoindolyl, dihydroquinazolinyl (such as 3,4-dihydro-4-oxo-quinazolinyl), tetrahydroquinolinyl (such as 1,2,3,4-tetrahydroquinolinyl), tetrahydroisoquinolinyl(such as 1,2,3,4-tetrahydroisoquiunolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isoindolyl, tetrahydroindoazolyl (such as 4,5,6,7-tetrahydroindazolyl), isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl,

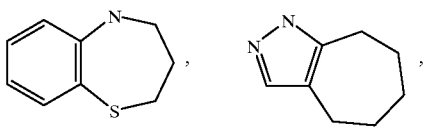

and the like.

Exemplary tricyclic heterocylclic groups include acridinyl, phenoxazinyl, phenazinyl, phenothiazinyl, carbozolyl, perminidinyl, phenanthrolinyl, carbolinyl, naphthothienyl, thianthrenyl, and the like.

Preferred heterocyclyl groups include morpholinyl, piperidinyl, piperazinyl, pyrrolidinyl, pyrimidinyl, pyridyl, pyrrolyl, imidazolyl, oxazolyl, isoxazolyl, acridinyl, azepinyl, hexahydroazepinyl, azetidinyl, indolyl, isoindolyl, thiazolyl, thiadiazolyl, quinolinyl, isoquinolinyl, 1,2,3,4-tetrahydroquinolinyl, 1,3,4-trihydroisoquinolinyl, 4,5,6,7-tetrahydroindadolyl, benzoxazinyl, benzoaxzolyl, benzthiazolyl, benzimidazolyl,

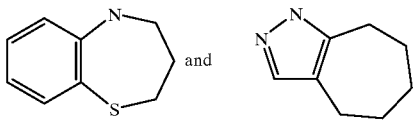

tetrazolyl, oxadiazolyl,

As used herein, unless otherwise noted, the term "heterocyclyl-alkyl" or "heterocyclyl-alkylene" shall denote any alkyl group substituted with a heterocyclyl group, wherein the heterocycly-alkyl group is bound through the alkyl portion to the central part of the molecule. Suitable examples of heterocyclyl-alkyl groups include, but are not limited to piperidinylmethyl, pyrrolidinylmethyl, piperidinylethyl, piperazinylmethyl, pyrrolylbutyl, piperidinylisobutyl, pyridylmethyl, pyrimidylethyl, and the like.

When a particular group is "substituted" (e.g., alkyl, alkylene, cycloalkyl, aryl, heterocyclyl, heteroaryl), that group may have one or more substituents, preferably from one to five substituents, more preferably from one to three substituents, most preferably from one to two substituents, independently selected from the list of substituents.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Under standard nomenclature used throughout this disclosure, the terminal portion of the designated side chain is described first, followed by the adjacent functionality toward the point of attachment. Thus, for example, a "phenyl (alkyl)amido(alkyl)" substituent refers to a group of the formula

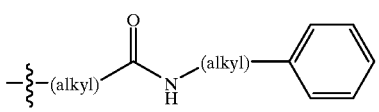

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes prevention, inhibition of onset, or alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Abbreviations used in the specification, particularly in the Schemes and Examples, are as follows:

| | |
|---|---|
| DBAD = | di-tert-butyl azodicarboxylate |
| DCE = | 1,2-dichloroethane |
| DCM = | dichloromethane |
| DEAD = | diethyl azodicarboxylate |
| DMA = | N,N-dimethylacetamide |
| DMAP = | 4-N,N-dimethylamino-pyridine |
| DME = | 1,2-dimethoxyethane |
| DMF = | dimethylformamide |
| DMSO = | dimethylsulfoxide |
| RT = | room temperature |
| TEA = | triethylamine |
| TFA = | trifluoroacetic acid |
| THF = | tetrahydrofuran |

The next section describes the compounds provided by the invention in more detail.

B. Compounds

The invention features compounds of formula (I) as described, for example, in the above Summary section and in the claims. Preferred compounds include those wherein:

(a) each of $G_a$ and $G_b$ is independently $NR_{3a}R_{4a}$ or $NR_{3b}R_{4b}$, respectively, or pyrrolidinyl, imidazolidinyl, pyrazolidinyl, piperidyl, isoindolinyl, morpholinyl, piperazinyl, imidazolyl, thiazolinyl, 5,6-dihydro-3-imidazo[2,1-B]thiazolyl, or thiazolyl; wherein each of $R_{3a}$, $R_{4a}$, $R_{3b}$ and $R_{4b}$ is independently selected from H, $C_{1-8}$ alkyl, $C_{3-7}$ cycloalkyl, and $(C_{3-7}$ cycloalkyl$)C_{1-6}$ alkyl;

(b) wherein X, is $L_aG_a$;

(c) $X_2$ is $L_bG_b$;

(d) $X_1$ is $L_aG_a$ and $X_2$ is $L_bG_b$;

(e) $X_1$ and $X_2$ are independently selected from pyrrolidinylmethyl, piperidylmethyl, di($C_{1-2}$ alkyl)amino ($C_{2-5}$ alkyl), and di($C_{1-2}$ alkyl)amino($C_{2-5}$ alkoxy);

(f) $X_1$ is selected from $G_a$, $R_aG_a$, or $R_aL_aG_a$;

(g) $X_2$ is selected from $G_b$, $R_bG_b$, or $R_bL_bG_b$;

(h) $X_1$ and $X_2$ are the same;

(i) each of $G_a$ and $G_b$ is independently $NR_3R_4$, pyrrolidinyl, imidazolidinyl, pyrazolidinyl, piperidyl, isoindolinyl, morpholinyl, thiazolyl, thiazolinyl, 5,6-dihydro-3-imidazo[2,1-B]thiazolyl, or piperazinyl; where $R_3$ and $R_4$ are each independently selected from H and $C_{1-4}$ alkyl;

(j) Y is O, S, $SO_2$, C=O, $CH_2$, $OCH_2$, $CH_2O$, or $NR_c$, wherein $R_c$ is H, $C_{1-8}$ alkyl, $C_{3-7}$ cycloalkyl, $(C_{3-7}$ cycloalkyl$)C_{1-6}$ alkyl, $C_{2-5}$ heterocyclyl, ($C_{2-7}$ heterocyclyl$)C_{1-6}$ alkyl, phenyl, (phenyl)$C_{1-4}$ alkyl, or [di ($C_{1-4}$ alkyl)amino]$C_{1-6}$ alkyl; or (k) combinations of the above.

The invention provides compounds such as: 1-[(4-(4-Pyrrolidin-1-ylmethyl-phenyl)-thiophen)-2-ylmethyl]-pyrrolidine; 1-[(4-(4-Pyrrolidin-1-ylmethyl-phenyl)-furan)-2-ylmethyl]-pyrrolidine; 1-((4-(4-Pyrrolidin-1-ylmethyl-thiophen)-2-ylthiophen)-2-ylmethyl)-pyrrolid ine; 1-[(2-(4-Pyrrolid in-1-ylmethyl-phenyl)-thiophen)-3-ylmethyl]-pyrrolidine; 1-[(3-(4-Pyrrolidin-1-ylmethyl-phenyl)-thiophen)-2-ylmethyl]-pyrrolidine; and 1-((4-(4-Pyrrolidin-1-ylmethyl-pyridin)-2-ylpyridin)-2-ylmethyl)-pyrrolidine.

Additional compounds of the invention include: 1-[4-(3,5-Dichloro-phenoxy)-benzyl]-pyrrolidine; 1-[4-(4-Piperidine-phenylsulfanyl)-3-nitro-benzyl]-piperidine; 4'-Pyrrolidin-1 -ylmethyl-biphenyl-4-carbaldehyde; 4'-Pyrrolidin-1-ylmethyl-biphenyl-4-carbaldehyde oxime; 3-Pyrrolid in-1-ylmethyl-1-(4-pyrrolid in-1-ylmethyl-benzyl)-1H-pyrrole; and 2-Pyrrolidin-1-ylmethyl-1-(4-pyrrolidin-1-ylmethyl-benzyl)-1H-pyrrole.

Further examples of compounds include: 1-[4-(4-Pyrrolidin-1-ylmethyl-phenoxy)-benzyl]-pyrrolidine; 1-[4-(4-Piperidin-1-ylmethyl-phenoxy)-benzyl]-piperidine; 1-[4-(4-Pyrrolidin-1-ylmethyl-benzenesulfonyl)-benzyl]-pyrrolidine; 1-[4-(4-Pyrrolidin-1-ylmethyl-benzyl)-benzyl]-pyrrolidine; 1-[4-(4-Imidazo-1-ylmethyl-phenoxy)-benzyl]-imidazole; 1-[4-(4-Imidazo-1-ylmethyl-benzyl)-benzyl]-imidazole; [4-(N, N'-dimethyl-isothiourea)-methyl-phenoxy)-benzyl]-N, N'-dimethyl-isothiourea; [4-(N-methyl-isothiourea)-methyl-phenoxy)-benzyl]-N-methyl-isothiourea; 2-[4-(4-(2-Imidazolidin)-2-ylthiomethyl-phenoxy)-benzyl-thio]-2-imidazolidine; 2-[4-(4-(2-Thiazolin)-2-ylthiomethyl-phenoxy)-benzyl-thio]-2-thiazoline; 2-[4-(4-(1-Methyl-imidazo)-2-ylthiomethyl-phenoxy)-benzyl-thio]-1-methyl-imidazole; 2-[4-(4-(2-Imidazolidin)-2-ylaminomethyl-phenoxy)-benzyl-amino]-2-imidazolidine and 1-(2-{4-[2-(1-phenethyl-pyrrolidine)-ethyl]-phenyl}-ethyl)-pyrrolidine.

Additional compounds include: (A) 1-[4-(4-Bromo-benzyloxy)-benzyl]-pyrrolidine; 1-[4-(4-Pyrrolidin-1-ylmethyl-phenoxymethyl)-benzyl]-1H-pyrrole; and 1-(4-Pyrrolidin-1-ylmethyl-benzyl)-1H-pyrrole; (B) Benzyl-(4-pyrrolid in-1-ylmethyl-phenyl)-amine; Benzyl-bis-(4-pyrrolidin-1-ylmethyl-phenyl)-amine; (3-Piperidin-1-yl-propyl)-bis-(4-pyrrolidin-1-ylmethyl-phenyl)-amine; and (2-(N,N-dimethylamine)ethyl)-bis-(4-pyrrolidin-1-ylmethyl-phenyl)-amine; and 3-[4-(4-(5,6-Dihydro-3-imidiazo[2,1-B]thiazol)-3-ylphenoxy)-phenyl]-(5,6-dihydro-3-imidiazo[2,1-B]thiazole); (D) Bis-[4-(3-dimethylamino-propylsulfanyl)-phenyl]-methanone dihydrochloride; Bis-[4-(3-dimethylamino-propoxy)-phenyl]-methanone; [4-(3-Dimethylamino-propoxy)-phenyl]-(4-hydroxy-phenyl)-methanone; and (E) Bis-[4-(2-dimethylamino-ethoxy)-phenyl]-methanone.

The invention also provides compounds that are useful as synthetic intermediates of the compounds of the invention. Such compounds, which themselves may or may not have pharmaceutical activity, include those provided in the schemes and synthetic examples.

The invention also contemplates compounds of the invention that have been isotopically modified to be detectable by positron emission tomography (PET) or single-photon emission computed tomography (SPECT), and methods of studying disorders mediated by the histamine $H_3$ receptor, comprising using an $^{18}$F-labeled compound of claim 1 as a positron emission tomography (PET) molecular probe.

During any of the processes for preparation of the compounds of the present invention, it may be necessary and/or desirable to protect sensitive or reactive groups on any of the molecules concerned. In addition, compounds of the invention may be modified by using protecting groups; such compounds, precursors, or prodrugs are also within the scope of the invention. This may be achieved by means of conventional protecting groups, such as those described in "Protective Groups in Organic Chemistry", ed. J. F. W. McOmie, Plenum Press, 1973; and T. W. Greene & P. G. M. Wuts, "Protective Groups in Organic Synthesis", 3$^{rd}$ ed., John Wiley & Sons, 1999. The protecting groups may be removed at a convenient subsequent stage using methods known from the art.

Hydroxyl Protecting Groups

Protection for the hydroxyl group includes methyl ethers, substituted methyl ethers, substituted ethyl ethers, substitute benzyl ethers, and silyl ethers.

Substituted Methyl Ethers

Examples of substituted methyl ethers include methyoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S, S-dioxido, 1-[(2-chloro-4-methyl)phenyl]-4-methoxypiperid in-4-yl, 1,4-dioxan-2-yl, tetrahydrofuranyl, tetrahydrothiofuranyl and 2,3,3a,4,5,6,7,7a-octahydro-7,8,8-trimethyl-4,7-methanobenzofuran-2-yl.

Substituted Ethyl Ethers

Examples of substituted ethyl ethers include 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, and benzyl.

Substituted Benzyl Ethers

Examples of substituted benzyl ethers include p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p, p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyidiphenylmethyl, 4,4',4"-tris(4,5-dichlorophthalimidophenyl)methyl 4,4',4"-tris (levulinoyloxyphenyl)methyl, 4,4',4"-tris(benzoyloxyphenyl)methyl, 3-(lmidazol-1-ylmethyl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, and benzisothiazolyl S,S-dioxido.

Silyl Ethers

Examples of silyl ethers include trimethylsilyl, triethylsilyl, triisopropylsilyl, dimethylisopropylsilyl, diethylisopropylsilyl, dimethylthexylsilyl, t-butyidimethylsilyl, t-butyldiphenylsilyl, tribenzylsilyl, tri-p-xylylsilyl, triphenylsilyl, diphenylmethylsilyl, and t-butylmethoxyphenylsilyl.

Esters

In addition to ethers, a hydroxyl group may be protected as an ester. Examples of esters include formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate(levulinate), 4,4-(ethylenedithio)pentanoate, pivaloate, adamantoate, crotonate, 4-methoxycrotonate, benzoate, p-phenylbenzoate, 2,4,6-trimethylbenzoate(mesitoate)

Carbonates

Examples of carbonates include methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, and methyl dithiocarbonate.

Assisted Cleavage

Examples of assisted cleavage include 2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, and 2-(methylthiomethoxymethyl)benzoate.

Miscellaneous Esters

Examples of miscellaneous esters include 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate (tigloate), o-(methoxycarbonyl)benzoate, p-P-benzoate, α-naphthoate, nitrate, alkyl N,N,N',N'-tetramethylphosphorodiamidate, N-phenylcarbamate, borate, dimethylphosphinothioyl, and 2,4-dinitrophenylsulfenate Sulfonates Examples of sulfonates include sulfate, methanesulfonate (mesylate), benzylsulfonate, and tosylate.

PROTECTION FOR 1,2- AND 1,3-DIOLS

Cyclic Acetals and Ketals

Examples of cyclic acetals and ketals include methylene, ethylidene, 1-t-butylethylidene, I-phenylethylidene, (4-methoxyphenyl)ethylidene, 2,2,2-trichloroethylidene, acetonide (isopropylidene), cyclopentylidene, cyclohexylidene, cycloheptylidene, benzylidene, p-methoxybenzylidene, 2,4-dimethoxybenzylidene, 3,4-dimethoxybenzylidene, and 2-nitrobenzylidene.

Cyclic Ortho Esters

Examples of cyclic ortho esters include methoxymethylene, ethoxymethylene, dimethoxymethylene, 1-methoxyethylidene, 1-ethoxyethylidine, 1,2-dimethoxyethylidene, α-methoxybenzylidene, 1-(N, N-dimethylamino)ethylidene derivative, α-(N,N-dimethylamino)benzylidene derivative, and 2-oxacyclopentylidene.

Silyl Derivatives

Examples of silyl derivatives include di-t-butylsilylene group, and 1,3-(1,1,3,3-tetraisopropyldisiloxanylidene) derivative.

AMINO PROTECTING GROUPS

Protection for the amino group includes carbamates, amides, and special-NH protective groups.

Examples of carbamates include methyl and ethyl carbamates, substituted ethyl carbamates, assisted cleavage carbamates, photolytic cleavage carbamates, urea-type derivatives, and miscellaneous carbamates.

Carbamates

Examples of methyl and ethyl carbamates include methyl and ethyl, 9-fluorenylmethyl, 9-(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, and 4-methoxyphenacyl.

Substituted Ethyl

Examples of substituted ethyl carbamates include 2,2,2-trichloroethyl, 2-trimethylsilylethyl, 2-phenylethyl, 1-(1-adamantyl)-1-methylethyl, 1,1-dimethyl-2-haloethyl, 1,1-dimethyl- 2,2- dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl and diphenylmethyl.

Assisted Cleavage

Examples of assisted cleavage include 2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1 -dimethyl-2-cyanoethyl, m-chloro-p-acyloxybenzyl, p-(dihydroxyboryl)benzyl, 5-benzisoxazolylmethyl, and 2-(trifluoromethyl)-6-chromonylmethyl.

Photolytic Cleavage

Examples of photolytic cleavage include m-nitrophenyl, 3,5-dimethoxybenzyl, o-nitrobenzyl, 3,4-dimethoxy-6-nitrobenzyl, and phenyl(o-nitrophenyl)methyl.

Urea-Type Derivatives

Examples of urea-type derivatives include phenothiazinyl-(10)-carbonyl derivative, N'-p-toluenesulfonylaminocarbonyl, and N'-phenylaminothiocarbonyl.

Miscellaneous Carbamates

Examples of miscellaneous carbamates include t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido)propyl, 1,1-dimethylpropynyl, di(2-pyridyl)methyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(3,5-dimethoxyphenyl) ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, and 2,4,6-trimethylbenzyl.

Examples of amides include:

Amides

N-formyl, N-acetyl, N-chloroacetyl, N-trichloroacetyl, N-trifluoroacetyl, N-phenylacetyl, N-3-phenylpropionyl, N-picolinoyl, N-3-pyridylcarboxamide, N-benzoylphenylalanyl derivative, N-benzoyl, N-p-phenylbenzoyl.

Assisted Cleavage

N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl) propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine derivative, N-o-nitrobenzoyl, N-o-(benzoyloxymethyl)benzoyl, and 4,5-diphenyl-3-oxazolin-2-one.

Cyclic Imide Derivatives

N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3,5-triazacyclohexan-2-one, and 1-substituted 3,5-dinitro-4-pyridonyl.

SPECIAL—NH PROTECTIVE GROUPS

Examples of special NH protective groups include:

N-Alkyl and N-Aryl Amines N-methyl, N-allyl, N-[2-(trimethylsilyl)ethoxy]methyl, N-3-acetoxypropyl, N-(1-isopropyl-4-nitro-2-oxo-3-pyrrolin-3-yl), quaternary ammonium salts, N-benzyl, N-4-methoxybenzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, and N-2-picolylamine N'-oxide.

Imine Derivatives

N-1,1-dimethylthiomethylene, N-benzylidene, N-p-methoxybenzylidene, N-diphenylmethylene, N-[(2-pyridyl) mesityl]methylene, and N-(N',N'-dimethylaminomethylene).

PROTECTION FOR THE CARBONYL GROUP

Acyclic Acetals and Ketals

Examples of acyclic acetals and ketals include dimethyl, bis(2,2,2-trichloroethyl), dibenzyl, bis(2-nitrobenzyl) and diacetyl.

Cyclic Acetals and Ketals

Examples of cyclic acetals and ketals include 1,3-dioxanes, 5-methylene-1,3-dioxane, 5,5-dibromo-1,3-dioxane, 5-(2-pyridyl)-1,3-dioxane, 1,3-dioxolanes, 4-bromomethyl-1,3-dioxolane, 4-(3-butenyl)-1,3-dioxolane, 4-phenyl-1,3-dioxolane, 4-(2-nitrophenyl)-1,3-dioxolane, 4,5-dimethoxymethyl-1,3-dioxolane, O,O'-phenylenedioxy and 1,5-dihydro-3H-2,4-benzodioxepin.

Acyclic Dithio Acetals and Ketals

Examples of acyclic dithio acetals and ketals include S,S'-dimethyl, S,S'-diethyl, S,S'-dipropyl, S,S'-dibutyl, S,S'-dipentyl, S,S'-diphenyl, S,S'-dibenzyl and S,S'-diacetyl.

Cyclic Dithio Acetals and Ketals

Examples of cyclic dithio acetals and ketals include 1,3-dithiane, 1,3-dithiolane and 1,5-dihydro-3H-2,4-benzodithiepin.

Acyclic Monothio Acetals and Ketals

Examples of acyclic monothio acetals and ketals include O-trimethylsilyl-S-alkyl, O-methyl-S-alkyl or -S-phenyl and O-methyl-S-2-(methylthio)ethyl.

Cyclic Monothio Acetals and Ketals

Examples of cyclic monothio acetals and ketals include 1,3-oxathiolanes.

MISCELLANEOUS DERIVATIVES

O-Substituted Cyanohydrins

Examples of O-substituted cyanohydrins include O-acetyl, O-trimethylsilyl, O-1-ethoxyethyl and O-tetrahydropyranyl.

Substituted Hydrazones

Examples of substituted hydrazones include N,N-dimethyl and 2,4-dinitrophenyl.

Oxime Derivatives

Examples of oxime derivatives include O-methyl, O-benzyl and O-phenylthiomethyl.

Imines

Substituted Methylene Derivatives, Cyclic Derivatives

Examples of substituted methylene and cyclic derivatives include oxazolidines, 1-methyl-2-(1'-hydroxyalkyl)

imidazoles, N,N'-dimethylimidazolidines, 2,3-dihydro-1,3-benzothiazoles, diethylamine adducts, and methylaluminum bis(2,6-di-t-butyl-4-methylphenoxide)(MAD)complex.

Monoprotection of Dicarbonyl Compounds

Selective Protection Of α-and β-Diketones

Examples of selective protection of α-and β-diketones include enamines, enol acetates, enol ethers, methyl, ethyl, i-butyl, piperidinyl, morpholinyl, 4-methyl-1,3-dioxolanyl, pyrrolidinyl, benzyl, S-butyl, and trimethylsilyl.

Cyclic Ketals, Monothio and Dithio Ketals

Examples of cyclic ketals, monothio and dithio ketals include bismethylenedioxy derivatives and tetramethylbismethylenedioxy derivatives.

Protection for the Carboxyl Group

Esters

Substituted Methyl Esters

Examples of substituted methyl esters include 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, phenacyl, p-bromophenacyl, α-methylphenacyl, p-methoxyphenacyl, carboxamidomethyl, and N-phthalimidomethyl.

2-Substituted Ethyl Esters

Examples of 2-substituted ethyl esters include 2,2,2-trichloroethyl, 2-haloethyl, ω-chloroalkyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl)ethyl, 2-(d iphenylphosphino)ethyl, 1-methyl-1-phenylethyl, t-butyl, cyclopentyl, cyclohexyl, allyl, 3-buten-1-yl, 4-(trimethylsilyl)-2-buten-1-yl, cinnamyl, α-methylcinnamyl, phenyl, p-(methylmercapto) phenyl and benzyl.

Substituted Benzyl Esters

Examples of substituted benzyl esters include triphenylmethyl, diphenylmethyl, bis(o-nitrophenyl)methyl, 9-anthrylmethyl, 2-(9,10-dioxo)anthrylmethyl, 5-dibenzosuberyl, 1-pyrenylmethyl, 2-(trifluoromethyl)-6-chromylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, piperonyl, 4-picolyl and p-P-benzyl.

Silyl Esters

Examples of silyl esters include trimethylsilyl, triethylsilyl, t-butyldimethylsilyl, i-propyidimethylsilyl, phenyidimethylsilyl and di-t-butylmethylsilyl.

Activated Esters

Examples of activated esters include thiols.

Miscellaneous Derivatives

Examples of miscellaneous derivatives include oxazoles, 2-alkyl-1,3-oxazolines, 4-alkyl-5-oxo-1,3-oxazolidines, 5-alkyl-4-oxo-1,3-dioxolanes, ortho esters, phenyl group and pentaaminocobalt(III) complex.

Stannyl Esters

Examples of stannyl esters include triethylstannyl and tri-n-butylstannyl.

AMIDES AND HYDRAZIDES

Amides

Examples of amides include N,N-dimethyl, pyrrolidinyl, piperidinyl, 5,6-dihydrophenanthridinyl, o-nitroanilides, N-7-nitroindolyl, N-8-Nitro-1,2,3,4-tetrahydroquinolyl, and p-P-benzenesulfonamides.

Hydrazides

Examples of hydrazides include N-phenyl and N,N'-diisopropyl.

The compounds of the invention can be prepared according to the methods described in the next section.

C. Synthesis

The compounds of the invention can be prepared according to traditional synthetic organic methods and matrix or combinatorial chemistry methods, as shown in Schemes 1-7 below and in Examples 1-34. A person of ordinary skill will be aware of variations and adaptations of the schemes and examples provided to achieve the compounds of the invention. One skilled in the art will recognize that synthesis of the compounds of the present invention may be effected by purchasing intermediate or protected intermediate compounds described in any of the schemes disclosed herein.

Compounds of formula I may be prepared according to the processes outlined in Schemes 1 through 5.

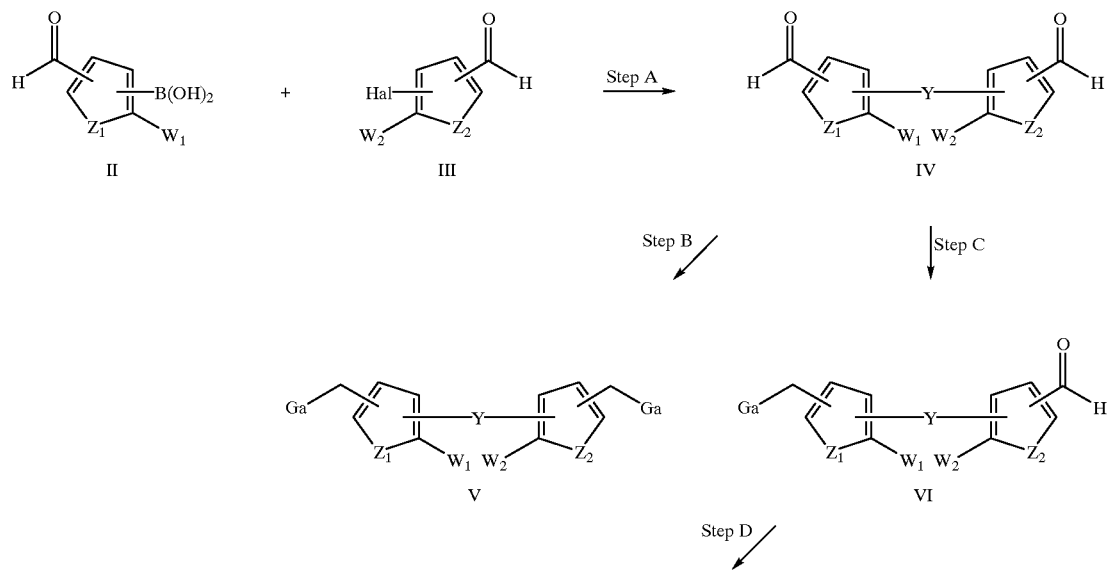

Scheme 1

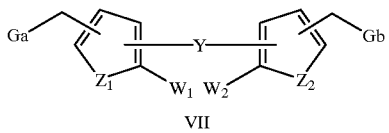

VII

Compounds of formula V and formula VII, wherein the substituents are as defined in formula I, may be prepared according to the process outlined in Scheme 1. Specifically compounds of formula II and formula III react to provide a compound of formula IV in Step A upon treatment with Pd catalyst such as $Pd_2(dba)_3$, a ligand such as triphenylphosphine, or t-tributylphosphine, in presence of a base, for example cesium carbonate, potassium carbonate or the like in a solvent such as dioxane, or THF. In a preferred embodiment the compounds of formula II and III react in presence of $Pd_2(dba)_3$, t-tributylphosphine, cesium carbonate in dioxane to afford a compound of formula IV. In Step B a compound of formula IV upon treatment with an appropriately Ga-H, where Ga is the defined substituents Ga in formula I, in the presence of a reductant such as $NaBH_4$, or $NaB(OAc)_3H$ in acidic condition, for example HOAc, in methylene chloride provides a compound of formula V. In a preferred embodiment the reductant is $NaB(OAc)_3H$.

A compound of formula VI may be obtained, in Step C, by reacting a compound of formula IV with an appropriately amount of Ga-H, where Ga is the defined substituents Ga in formula I. The reaction condition is same as that of for a compound of formula V except the amount of Ga-H is a half of that for a compound of formula V.

A compound of formula VII may be obtained, in Step D, by treating a compound of formula of VI with Gb-H where Gb is the defined substituents Gb in formula I, in the presence of a reductant such as $NaBH_4$ or $NaB(OAc)_3H$ in acidic condition, for example in HOAc, in methylene chloride. A compound of formula VII may also be obtained, in Step D, by treating hydroxyamine, or alkylated hydroxyamine, in presence of a base such as cesium carbonate, potassium carbonate, sodium carbonate or the like in a solvent such as methanol, or ethanol. In a preferred embodiment a compound of formula VI is treated with hydroxyamine, and sodium carbonate in ethanol to afford a compound of formula VII.

Compounds of formula X and formula XII, wherein the substituents are as defined in formula I, may be prepared according to the process outlined in Scheme 2. Specifically a compound of formula VIII is converted to a compound of formula IX in Step E upon treatment with thionyl chloride, or oxalyl chloride in chloroform, dichloromethane, or dichloroethane at room temperature or an elevated temperature. In a preferred embodiment the compounds of formula VIII reacts with thionyl chloride in chloroform at 50-70° C. providing a compound of formula IX. In Step F a compound of formula IX upon treatment with an appropriately Ga-H, where Ga is the defined substituents Ga in formula 1, in the presence of a base, for example cesium carbonate, potassium carbonate, sodium carbonate or the like in a solvent such as acetone, or acetonitrile provides a compound of formula X. In a preferred embodiment, the base is potassium carbonate and the solvent is acetonitrile.

A compound of formula of IX in Step G reacts with phthalimide, in presence of a base, for example cesium carbonate, potassium carbonate, sodium carbonate or the like in DMF to afford an intermediate. In a preferred embodiment the base is potassium carbonate. The intermediate may react with hydrazine in a mixture of methanol and THF at elevated temperature preferably at the boiling point of the mixed solvents providing a compound of formula XI.

A compound of formula XI is converted to a compound of formula XII in Step H upon treatment with an appropriately isothiourea, or alkylated isothiourea in pyridine at reflux temperature. In a preferred embodiment the compound of formula XI reacts with 2-thio-2-imidazoline in pyridine at reflux providing a compound of formula IX.

Scheme 2

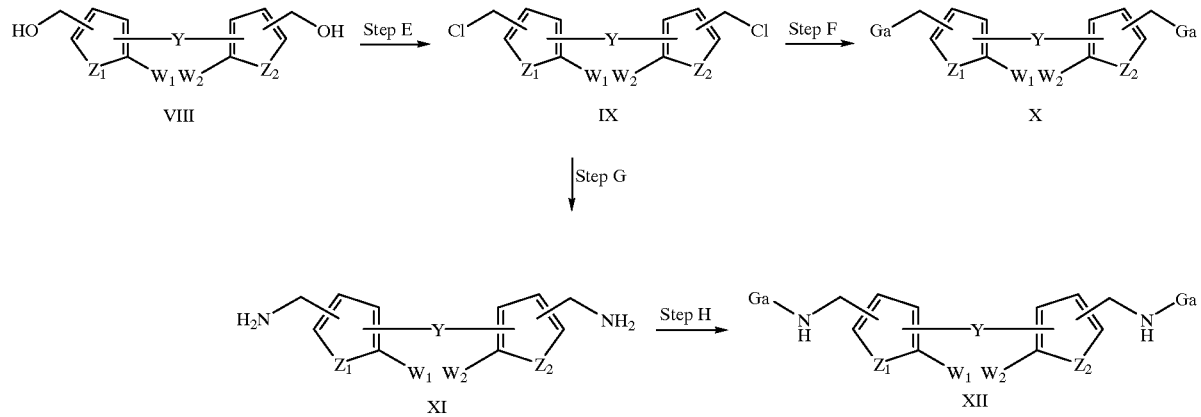

Scheme 3

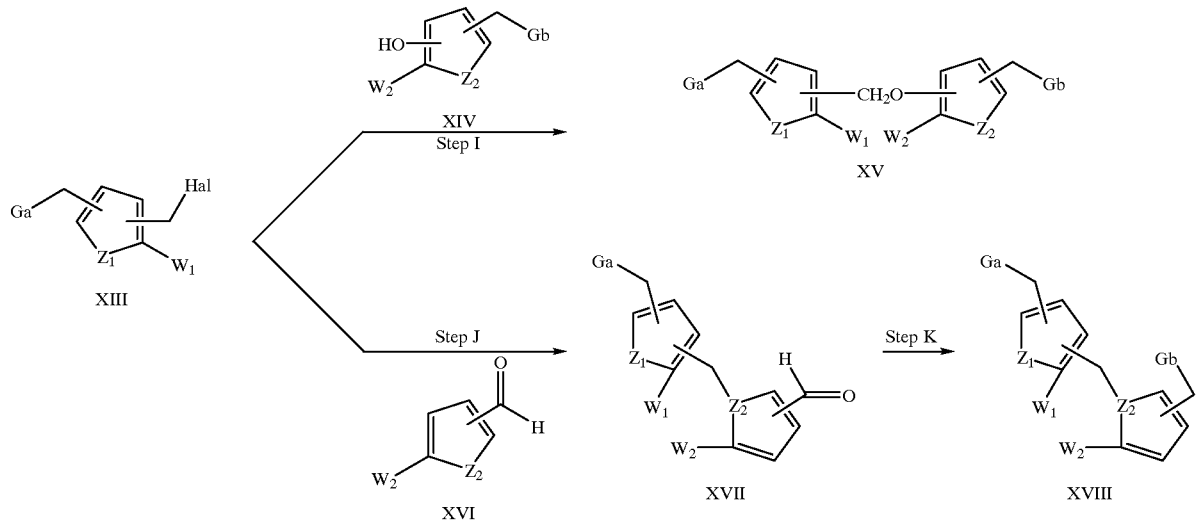

Compounds of formula XV and formula XVIII, wherein the substituents are as defined in formula I, may be prepared according to the process outlined in Scheme 3. Specifically a compound of formula XIII is converted to a compound of formula XV in Step I by reacting with a compound of formula XIV in the presence of a base, for example sodium t-butoxide, potassium t-butoxide, cesium carbonate, potassium carbonate, sodium carbonate or the like in a solvent such as methanol, or ethanol. In a preferred embodiment, the base is t-butoxide and the solvent is ethanol.

A compound of formula of XIII in Step J reacts with a compound of formula of XVI, wherein $Z_2$ is nitrogen, in presence of tetrabutylammonium hydrogen sulfate, and a base for example cesium carbonate, potassium carbonate, or sodium hydroxide in a solvent such as benzene, or toluene to afford a compound of formula of XVII. In a preferred embodiment the base is sodium hydroxide, and the solvent is benzene.

A compound of formula XVIII may be obtained in Step K by treating a compound of formula XVII with an appropriately Ga-H, where Ga is the defined substituents Ga in formula I, in the presence of a reductant such as $NaBH_4$, or $NaB(OAc)_3H$ in acidic condition, for example HOAc, in methylene chloride. In a preferred embodiment the reductant is $NaB(OAc)_3H$.

Scheme 4

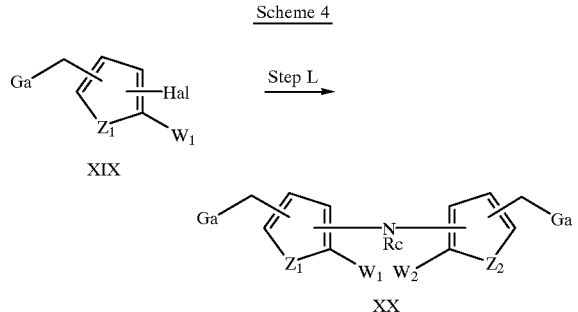

Compounds of formula XX wherein the substituents are as defined in formula I, may be prepared according to the process outlined in Scheme 4. Specifically a compound of formula XIX is converted to a compound of formula XX in step L upon treatment with amine $NHR_C$, which is $R_C$ is the defined substituents $R_C$ in compounds of formula I, Pd catalyst such as $Pd_2(dba)_3$, a ligand such as triphenylphosphine, or t-tributylphosphine, in presence of a base, for example cesium carbonate, potassium carbonate, or the like in a solvent such as dioxane, or THF. In a preferred embodiment the compound of formula XIX reacts with amine NHRC in the presence of $Pd_2(dba)_3$, t-tributylphosphine, cesium carbonate in dioxane to afford a compound of formula XX.

Scheme 5

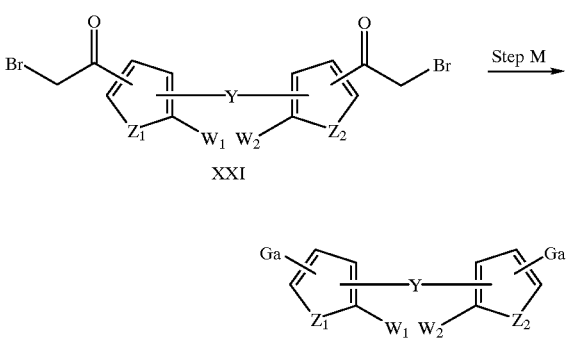

A compound of formula XXI in Step M is treated with an appropriately thiourea, or alkylated thiourea, in a solvent such as methanol or ethanol at reflux temperature for certain time like 1 or 2 hour. Subsequently a base such as triethylamine, cesium carbonate, potassium carbonate, or the like was treated providing a compound of formula XXII. In a preferred embodiment the compound of formula XXI reacts with 2-imidazolidinethione in ethanol at reflux followed by treating triethylamine to afford a compound of formula XXII.

Scheme 6

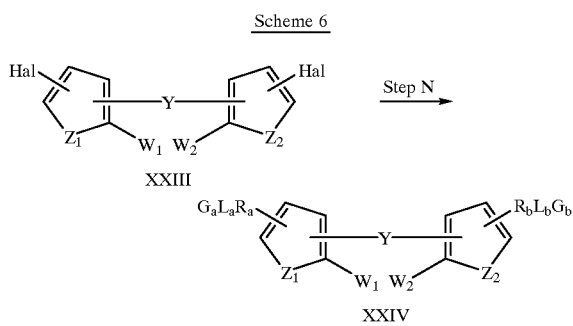

A compound of formula XXIII in Step N is treated with an appropriately dialkylamino-alkyl-thiol and a base such as sodium hydride in the presence of a catalyst such as $Pd(PPh_3)_4$ in a solvent such as n-butanol at reflux temperature for a certain time like 6 hours providing a compound of formula XXIV.

Scheme 7

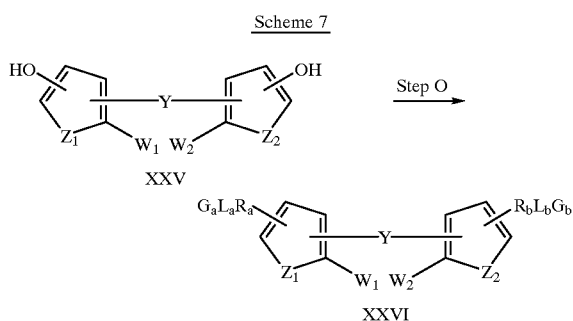

A compound of formula XXV in Step O is treated with an appropriately dialkylamino-alkyl-halogen and a base such as potasium t-butoxide in a solvent such as methanol or ethanol at reflux temperature for a certain time like 18 or 24 hours providing a compound of formula XXVI.

D. Formulation, Administration, and Therapy

The disclosed compounds, alone or in combination (with, for example, a histamine $H_1$ receptor antagonist), are useful for treating or preventing neurologic disorders including sleep/wake and arousal/vigilance disorders (e.g. insomnia and jet lag), attention deficit hyperactivity disorders (ADHD), learning and memory disorders, cognitive dysfunction, migraine, neurogenic inflammation, dementia, mild cognitive impairment (pre-dementia), Alzheimer's disease, epilepsy, narcolepsy, eating disorders, obesity, motion sickness, vertigo, schizophrenia, substance abuse, bipolar disorders, manic disorders and depression, as well as other histamine $H_3$ receptor mediated disorders such as upper airway allergic response, asthma, itch, nasal congestion and allergic rhinitis in a subject in need thereof.

1. Formulation and Administration

The compounds or compositions of the invention may be formulated and administered to a subject by any conventional route of administration, including, but not limited to, intravenous, oral, subcutaneous, intramuscular, intradermal and parenteral administration. The quantity of the compound which is effective for treating each condition may vary, and can be determined by one of ordinary skill in the art.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali ml salts, e.g., sodium or potassium salts; alkaline earth ml salts, e.g., calcium or magnesium salts; and salts formed with suitable organic ligands, e.g., quaternary ammonium salts.

Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts in vivo after administration to the patient. Conventional procedures for the selection and preption of suitable prodrug derivatives are described, for example, in "Design of Prodrugs", ed. H. Bundgaard, Elsevier, 1985. In addition to salts, the invention provides the esters, amides, and other protected or derivatized forms of the described compounds.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The present invention also provides pharmaceutical compositions comprising one or more compounds of this invention in association with a pharmaceutically acceptable carrier and optionally additional pharmaceutical agents such as $H_1$ antagonists or SSRIs. Preferably these compositions are in unit dosage forms such as pills, tablets, caplets, capsules (each including immediate release, timed release and sustained release formulations), powders, granules, sterile parenteral solutions or suspensions (including syrups and emulsions), metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules.

This solid preformulation composition is then subdivided into unit dosage forms of the type described above containing from 5 to about 1000 mg of the active ingredient of the present invention. Examples include 5 mg, 7 mg, 10 mg, 15 mg, 20 mg, 35 mg, 50 mg, 75 mg, 100 mg, 120 mg, 150 mg, and so on. The tablets or pills of the disclosed compositions can be coated or otherwise compounded to provide a dosage form affording the advantage of prolonged action. For example, the tablet or pill can comprise an inner dosage and an outer dosage component, the latter being in the form of an envelope over the former. The two components can be septed by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the compounds and compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of ADHD is required.

The daily dosage of the products may be varied over a wide range from 1 to 1,000 mg per adult human per day. For oral administration, the compositions are preferably provided in the form of tablets containing 1.0, 5.0, 10.0, 15.0, 25.0, 50.0, 100, 250 and 500 milligrams of the active ingredient for the symptomatic adjustment of the dosage to the subject to be treated. An effective amount of the drug is ordinarily supplied at a dosage level of from about 0.01 mg/kg to about 20 mg/kg of body weight per day. Preferably, the range is from about 0.02 mg/kg to about 10 mg/kg of body weight per day, and especially from about 0.05 mg/kg to about 10 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

2. Combination Therapy

The disclosed compounds are useful in combination with other therapeutic agents, including $H_1$ receptor antagonists, $H_2$ receptor antagonists, and neurotransmitter modulators such as SSRIs and non-selective serotonin re-uptake inhibitors (NSSRIs).

Methods are known in the art for determining effective doses for therapeutic and prophylactic purposes for the disclosed pharmaceutical compositions or the disclosed drug combinations, whether or not formulated in the same composition.

For therapeutic purposes, the term "jointly effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "jointly effective amount" refers to that amount of each active compound or pharmaceutical agent, alone or in combination, that inhibits in a subject the onset or progression of a disorder as being sought by a researcher, veterinarian, medical doctor or other clinician, the delaying of which disorder is mediated, at least in part, by the modulation of one or more histamine receptors. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both drugs are administered in an amount that is sub-therapeutic or sub-prophylactic if administered alone, but are therapeutic or prophylactic when administered together. Combinations of three or more drugs are analogously possible. Methods of combination therapy include co-administration of a single formulation containing all active agents; essentially contemporaneous administration of more than one formulation; and administration of two or more active agents separately formulated.

E. EXAMPLES

Example 1

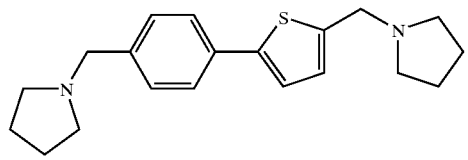

1[(4-(4-Pyrrolidin-1-ylmethyl-phenyl)-thiophen)-2-ylmethyl]-pyrrolidine $K_i$=9.0 nM Step A 2-Formyl-4-(4-formylphenyl)-thiophene 5-Formyl-2-thiophene boronic acid (1 equiv, 312 mg), 4-bromobenzaldehyde (1 equiv, 312 mg), Pd$_2$(dba)$_3$ (1.5% equiv, 28 mg), t-BU$_3$P (3.5% equiv, 15 mg), and cesium carbonate (1.3 g) in dioxane (2 mL) was stirred at 80° C. for 24 h. After concentration, the mixture was purified by preparative TLC (20% EtOAc in Hexanes) to afford the title compound (40 mg).

Step B

2-Formyl-4-(4-formylphenyl)-thiophene (1 equiv, 33 mg) mixed with prrolidine (2.6 equiv, 33 uL), HOAc (4 equiv, 35 uL), and NaBH(OAc)$_3$ (2.6 equiv, 103 mg) in methylene chloride (5 mL) was stirred at room temperature for 16 h. After concentration, the mixture was purified by preparative TLC (20% EtOAc in methylene chlorides) to afford the title compound (10 mg). $^1$H NMR (400 MHz, CDCl$_3$)δ7.45 (d, J=8.3 Hz, 2 H), 7.25 (d, J=8.3 Hz, 2 H), 7.06 (d, J=3.6 Hz, 1 H), 6.22 (d, J=3.6 Hz, 1 H), 3.76 (s, 2 H), 3.58 (s, 2 H), 2.51 (m, 8 H), 1.74 (m, 8 H).

Example 2

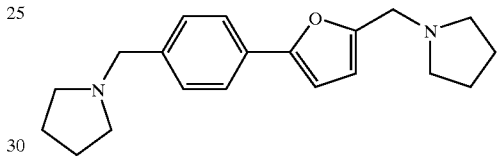

1-[(4-(4-Pyrrolidin-1-ylmethyl-phenyl)-furan)-2-ylmethyl]-pyrrolidine $K_i$=0.41 nM The title compound was prepared starting from 5-formyl-2-furan boronic acid and 4-bromobenzaldehyde by the same method described in Example 1.

$^1$H NMR (400 MHz, CDCl$_3$)δ7.55 (d, J=8.3 Hz, 2 H), 7.27 (d, J=8.3 Hz, 2 H), 6.50 (d, J=3.3 Hz, 1 H), 6.22 (d, J=3.3 Hz, 1 H), 3.69 (s, 2 H), 3.62 (s, 2 H), 2.55 (m, 8 H), 1.74 (m, 8 H).

Example 3

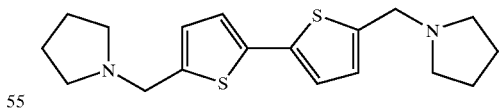

1-((4-(4-Pyrrolidin-1-ylmethyl-thiophen)-2-ylthiophen)-2-pyrrolidine $K_i$=1.4 nM The title compound was prepared starting from 5-formyl-2-thiophene boronic acid and 2-bromo-5-formylthiophene by the same method described in Example 1. $^1$H NMR (400 MHz, CDCl$_3$)δ7.06 (d, J=3.6 Hz, 2 H), 6.72 (s, J=3.6 Hz, 2 H), 3.65 (s, 4 H), 2.48 (s, 8 H), 1.64 (m, 8 H).

Example 4

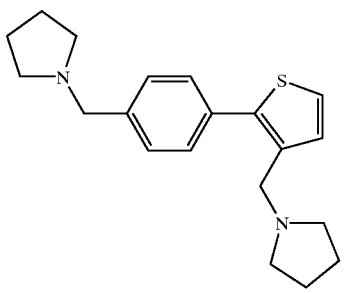

1-[(2-(4-Pyrrolidin-1-ylmethyl-phenyl)-thiophen)-3-ylmethyl]-pyrrolidine $K_i$=9.0 nM The title compound was prepared starting from 2-formyl-3-thiophene boronic acid and 4-bromobenzaldehyde by the same method described in Example 1. $^1$H NMR (400 MHz, CDCl$_3$)δ7.47 (m, 2 H), 7. 37 (m, 2 H), 7.21 (d,1 H), 6.16 (m,1 H), 3.55 (s, 2 H), 3.52 (s, 2 H), 2.44 (m, 8 H), 1.70 (m, 8 H).

Example 5

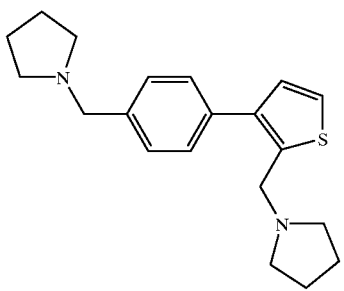

1-[(3-(4-Pyrrolidin-1-ylmethyl-phenyl)-thiophen)-2-ylmethyl]-pyrrolidine $K_i$=63 nM The title compound was prepared starting from 3-formyl-2-thiophene boronic acid and 4-bromobenzaldehyde by the same method described in Example 1. $^1$H NMR (400 MHz, CDCl$_3$)δ7.26 (m, 4 H), 6.50 (d, J=5.1 Hz, 1 H), 6.22 (d, J=5.1 Hz, 1 H), 3.77 (s, 2 H), 3.57 (s, 2 H), 2.48 (m, 8 H), 1.71 (m, 8 H).

Example 6

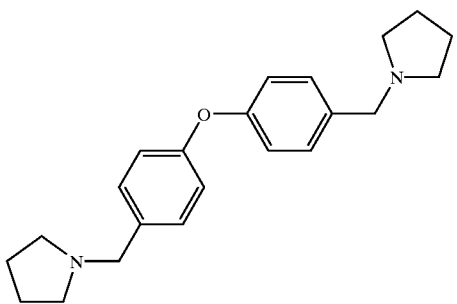

1-[(4-(4-Pyrrolidin-1-ylmethyl-phenoxy)-benzyl]-pyrrolidine $K_i$=0.50 nM

A suspension of 4,4-oxydibenzyl chloride (135 mg), pyrrolidine (107 mg), potassium carbonate (212 mg) and tetrabutylammonium iodide (5 mg) in acetonitrile (10 mL) was heated at reflux for 1 h. Then the solvent was evaporated. The residue was dissolved in methylene chloride, washed with saturated aqueous sodium bicarbonate, dried (sodium sulfate), and concentrated providing the title compound (168 mg). $^1$H NMR (400 MHz, CDCl$_3$)δ7.30 (d, J=10 Hz, 4 H), 7.27 (d, J=10 Hz, 4 H), 3.54 (s, 4 H), 2.55 (m, 8 H), 1.80 (m, 8 H).

Example 7

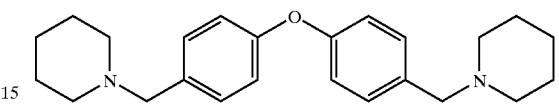

1-[(4-(4-Piperidin-1-ylmethyl-pheoxy)-benzyl]-piperidine $K_i$=0.66 nM

A suspension of 4,4-oxydibenzyl chloride (117 mg), piperidine (111 mg), potassium carbonate(180 mg) and tetrabutylammonium iodide (5 mg) in acetonitrile (10 mL) was heated at reflux for 1 h. Then the solvent was evaporated. The residue was dissolved in methylene chloride, washed with saturated aqueous sodium bicarbonate, dried (sodium sulfate), and concentrated providing the title compound (110 mg). M +H+(calculated):

365.3; M +H+(found): 365.1.$^1$H NMR (400 MHz, MeOH-d$_6$)δ7.21 (d, J=12 Hz, 4 H), 6.85 (d, J=12 Hz, 4 H), 3.40 (s, 4 H), 2.33 (m, 8 H), 1.50 (m, 8 H).

Example 8

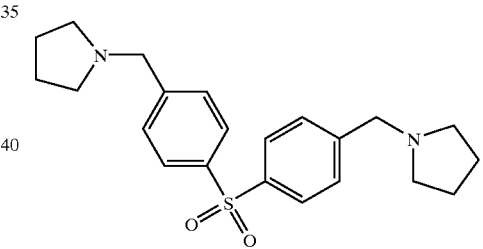

1-[(4-(4-Pyrrolidin-1-ylmethyl-benzenesulfonyl)-benzyl]-pyrrolidine $K_i$=2.5 nM Step A 4,4'-sulfonyldibenzyl chloride A solution of 4,4'-sulfonyldibenzyl alcohol (278 mg), and thionyl chloride (0.8 mL) in chloroform (10 mL) was heated at reflux for 2 h. Evaporation of solvent gave the title compound which was used without further purification.

Step B

A suspension of 4,4'-sulfonyldibenzyl chloride (157 mg), pyrrolidine (107 mg), potassium carbonate (212 mg) and tetrabutylammonium iodide (5 mg) in acetonitrile (10 mL) was heated at reflux for 1 h. Then the solvent was evaporated. The residue was dissolved in methylene chloride, washed with saturated aqueous sodium bicarbonate, dried (sodium sulfate), and concentrated. Preparative thin layer silica gel chromatography of the residue (10% methanol/dichloromethane) provided the title compound (110 mg).$^1$H NMR (400 MHz, CDCl$_3$)δ7.86 (d, J=8.5 Hz, 4 H), 7. 46 (d, J=8.5 Hz, 4 H), 3.61 (s, 4 H), 2.45 (m, 8 H), 1.75 (m, 8 H).

Example 9

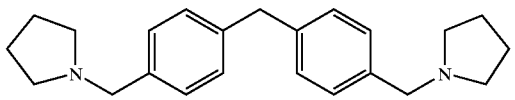

1-[(4-(4-Pyrrolidin-1-ylmethyl-benzyl)-benzyl]-pyrrolidine $K_i$=2.0 nM

The title compound was prepared starting from 4,4'-methylenedibenzyl chloride and pyrroline by the same method described in example 6. $^1$H NMR (400 MHz, CDCl$_3$)δ7.17 (d, J=8.0 Hz, 4 H), 7.05 (d, J=8.0 Hz, 4 H), 3.86 (s, 2 H), 2.42 (m, 8 H), 1.69 (m, 8 H).

Example 10

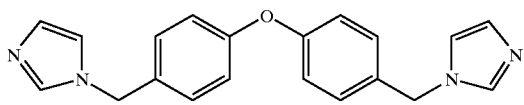

1-[(4-(4-Imidazo-1-ylmethyl-phenoxy)-benzyl]-imidazole $K_i$=151 nM

The title compound was prepared starting from 4,4'-oxydibenzyl chloride and imidazole by the same method described in example 6. $^1$H NMR (400 MHz, CDCl$_3$)δ7.63 (s, 2 H), 7.15 (d, J=8.6 Hz, 4 H), 6.99 (s, 2 H), 6.84 (d, J=8.5 Hz, 2 H), 5.07 (s, 4 H).

Example 11

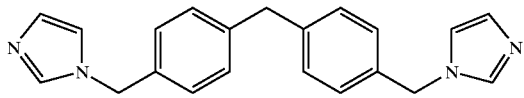

1-[(4-(4-Imidazo-1-ylmethyl-benzyl)-benzyl]-imidazole $K_i$=150 nM

The title compound was prepared starting from 4,4'-methylenedibenzyl chloride and imidazole by the same method described in example 6. $^1$H NMR (400 MHz, CDCl$_3$)δ7.45 (s, 2 H), 7.10 (d, J=8.0 Hz, 4 H), 6.88 (m, 6 H), 6.57 (s, 2 H), 5.02 (s, 4 H), 3.90 (s, 2 H).

Example 12

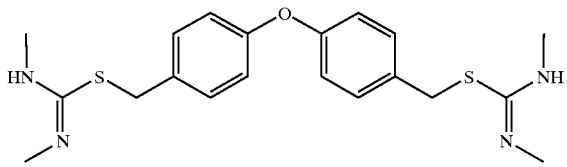

[4-(N-N'-dimethyl-isothiourea)-methyl-phenoxy-)-benzyl]-N,N'-dimethyl-isothiourea $K_i$=85 nM A mixture of 4,4-oxydibenzyl chloride (1equiv, 67 mg), and N, N'-dimethyl-thiourea (2equiv, 52 mg) in ethanol (10 mL) was heated at reflux for 8 h. Then the solvent was evaporated to provide the title compound 2HCl salt in quantitative yield. $^1$H NMR (400 MHz, MeOD-d$_4$)δ7.48 (m, 4 H), 7.04 (d, 4 H), 4.53 (m, 4 H), 3.07 (m, 12 H).

Example 13

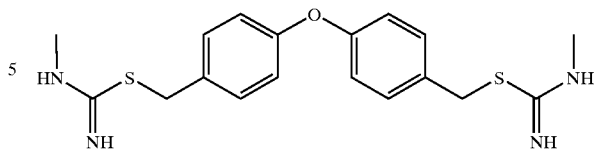

[4-(N-methyl-isothiourea)-methyl-phenoxy-)-benzyl]-N-methyl-isothiourea $K_i$=629 nM The title compound 2HCI salt was prepared starting from 4,4'-oxydibenzyl chloride and N-methyl-thiourea by the same method described in Example 12. $^1$H NMR (400 MHz, MeOD-d$_4$)δ7.46 (m, 4 H), 6.99 (m, 4 H), 4.49 (m, 4 H), 3.00 (m, 6 H),

Example 14

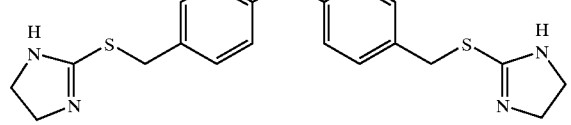

2-[4-(4-(2Imidazolin)-2-ylthiomethyl-phenoxy-)-benzyl-thio]-2-imidazolidone 4,4'-Oxydibenzyl chloride (67 mg) and -2-imidazlidinethion (51 mg) in ethanol (10 mL) were reflux for 2 hour. After cooled down, ether was added and precipitate was collected as the title compound 2HCl salts (80 mg). $^1$H NMR (400 MHz, MeOD-d$_4$)δ7.48 (d, J=8.7 Hz, 4 H), 7.04 (d, J=8.7 Hz, 4 H), 4.53 (s, 4 H), 4.00 (s, 8 H).

Example 15

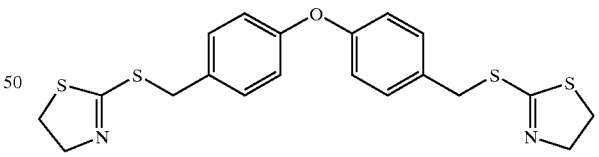

2-[4-(4-(2Thiazolin)-2-ylthiomethyl-phenoxy-)-benzyl-thio]-2-thiazoline $K_i$=2574 nM To a mixture of 4,4-oxydibenzyl chloride (1 equiv, 134 mg), and 2-thio-thiazoline (2 equiv, 119 mg) in ethanol (1 mL) was added NaOH (2.5 equiv, 50 mg) in H$_2$O (2 mL). After heated at 80° C. for 2 h. Concentration and preparative TLC (EtOAc in hexanes) provide the title compound (100 mg). $^1$H NMR (400 MHz, CDCl$_3$) δ7.24 (d, J=6.7 Hz, 4 H), 6.86 (d, J=6.7 Hz, 4 H), 4.25 (s, 4 H), 4.15 (t, J=8.0 Hz, 4 H), 3.30 (t, J=8.0 Hz, 4 H).

Example 16

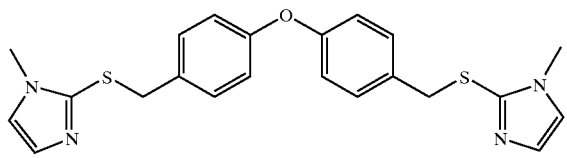

2-[4-(4-(1Methyl-imidazo)-2-ylthiomethyl-phenoxy-)-benzyl-thio]-1-methyl-imidazole $K_i$=792 nM The title compound was prepared starting from 4,4'-oxydibenzyl chloride and 1-methyl-2-thio-imidazole by the same method described in Example 15. $^1$H NMR (400 MHz, CDCl$_3$)δ7.14 (m, 6 H), 6.90 (m, 6 H), 4.19 (s, 4 H), 3.38 (m, 12 H).

Example 17

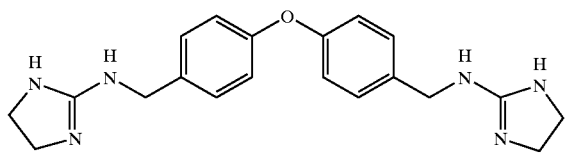

2-[4-(4-(2Imidazolin)-2-ylaminomethyl-phenoxy-)-benzyl-amino]-2-imidazolidone $K_i$=344 nM Step A 4,4'-oxydibenzyl amine The suspension of 4,4'-oxydibenzyl chloride (2.5 g), phthalimide (2.96 g), and potassium (6.76 g) was vigorously stirred at room temperature for 16 h. Water (100 mL) was added, and the precipitate was filtered. The solid was collected, dissolved in methylene chloride (200 mL), washed with 1N NaOH (2×100 mL), and dried. After concentration, the crude intermediate was obtained. This intermediate (1.22 g, 2.5 mmol) mixed with hydrazine (0.74 mL) in MeOH/THF (16 mL/16 mL) was heated at reflux. After overnight, the suspension was cooled, and filtered. The solid was washed with methanol. The filtrate was concentrated. The resulting solid was partitioned between methylene chloride (200 mL) and 1N NaOH (2×100 mL), washed, and dried. After concentration, the title compound was obtained (500 mg).

Step B

The 4,4'-oxydibenzyl amine (22 mg) and 2-thio-2-imidiazolidine were mixed in pyridine (4 mL). The mixture was heated at 100° C. for overnight. Then solvent was evaporated. Preparative TLC (EtOAc in hexanes) of the residue provided the title compound (16 mg). $^1$H NMR (400 MHz, MeOD-d$_4$)δ7.38 (m, 4 H), 7.02 (m, 4 H), 4.25 (s, 4 H), 3.77 (s, 8 H).

Example 18

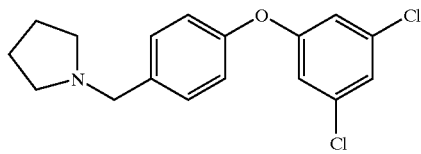

1-[4-(3,5-Dichloro-phenoxy)-benzyl]-pyrrolidine

The title compound was prepared starting from 4-(3,5-dichloro-phenoxy)-benzaldehyde and pyrrolidine by the same method (step B) described in Example 1. $^1$H NMR (400 MHz, CDCl$_3$)δ7.22 (t, J=7.8 Hz, 1 H), 7.07 (d, J=7.6 Hz,1 H), 6.96 (m, 2 H), 6.81 (m,1 H), 6.76 (m, 2 H), 3.52 (s, 2 H), 2.45 (m, 4 H), 1.70 (m, 4 H).

Example 19

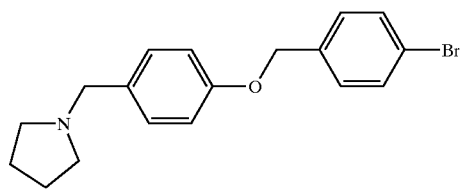

1-[4-(4-Bromo-benzyloxy)-benzyl]-pyrrolidine

Step A 4-Hydroxybenzyl-pyrrolidine

The title compound was prepared starting from 4-hydroxybenzaldehyde and pyrrolidine by the same method (step B) described in Example 1.

Step B

The mixture of 4-hydroxybenzyl-pyrrolidine (177 mg), 4-bromo-benzylchloride (205 mg), and t-Bu$_3$ONa (192 mg) in ethanol (10 mL) was heated at 80° C. for overnight. Concentration and preparative TLC provided the title compound (200 mg). $^1$H NMR (400 MHz, CDCl$_3$)δ7.50 (d, J=6.5 Hz, 2 H), 7.32 (d, J=6.5 Hz, 2 H), 7.25 (d, J=6.5 Hz, 2 H), 6.90 (d, J=6.5 Hz, 2 H), 2.84 (s, 2 H), 2.50 (m, 4 H), 1.42 (m, 4 H).

Example 20

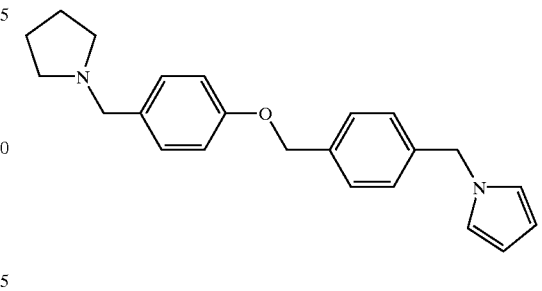

1-[4-(4Pyrrolidin1-ylmethyl-phenoxymethyl)-benzyl]-1H-pyrroleK$_i$=16 nM step A 1-(4-Chloromethyl-benzyl)-pyrrole The mixture of pyrrole (0.67 g), triethylamine (0.75 g), DMAP (0.09 g), and 4-chloromethyl-benzoyl chloride (1.399 g) was stirred at room temperature for overnight. After concentration, column chromatography (EtOAc in hexanes) provided the desired intermediate. This intermediate (110 mg) in THF (2 mL) was treated with BF$_3$Et$_2$O (0.5 mL) and NaBH$_4$ (76 mg). After being heated at 80° C. for overnight, the reaction was quenched by NaHCO$_3$ saturated solution. The organic layer was concentrated and preparative TLC to provide the title compound.

Step B

The title compound was prepared starting from 1-(4-chloromethyl-benzyl)-pyrrole and 4-hydroxybenzyl-pyrrolidine by the same method described in Example 19. $^1$H NMR (400 MHz, MeOD-d$_4$)δ7.18 (m, 2 H), 6.99 (m, 2 H), 6.59 (t, J=2.1 Hz, 2 H), 5.97 (t, J=2.1 Hz, 2 H), 4.99 (s, 2 H), 3.55 (s, 2 H), 2.41 (m, 4 H), 1.70 (m, 4 H).

Example 21

1-(4Pyrrolidin1-ylmethyl-benzyl)-1H-pyrrole

The title compound was prepared starting from 1-(4-chloromethyl-benzyl)-pyrrole (preparation in example 20 step A) and pyrrolidine by the same method reported in Example 19 step B. $^1$H NMR (400 MHz, MeOD-d$_4$) δ7.26 (m, 2 H), 7.15 (m, 2 H), 7.05 (m, 2 H), 6.85 (m, 2 H), 6.57 (t, J=2.1 Hz, 2 H), 5.96 (t, J=2.1 Hz, 2 H), 4.98 (s, 2 H), 4.92 (s, 2 H), 3.50 (s, 3 H), 2.50 (m, 2 H), 1.70 (m, 2 H).

Example 22

Benzyl-(4pyrrolidin1-ylmethyl-phenyl)-amine

Step A 4-Bromobenzyl-pyrrolidine

The title compound was prepared starting from 4-bromobenzaldehyde and pyrrolidine by the same method (step B) described in Example 1.

Step B

The mixture of 4-bromobenzyl-pyrrolidine (1 equiv, 120 mg), Pd$_2$(dba)$_3$ (2.0% equiv, 9.15 mg), t-Bu$_3$P (1.6% equiv, 1.6 mg), benzylamine (1 equiv, 53.6 mg) and NaOtBu$_3$ (1.5 equiv, 72 mg) in toluene (5 mL) was heated at 70° C. for 8 h.

Concentration and preparative TLC provided the title compound (80 mg). $^1$H NMR (400 MHz, CDCl$_3$) δ7.36 (m, 5 H), 7.17 (d, J=8.4 Hz, 2 H), 6.62 (d, J=8.4 Hz, 2 H), 4.34 (s, 2 H), 3.60 (s, 2 H), 2.59 (m, 4 H), 1.83 (m, 4 H).

Example 23

Benzyl-bis-(4pyrrolidin1-ylmethyl-phenyl)-amine K$_i$=15 nM

Step A 4-Bromobenzyl-pyrrolidine

The title compound was prepared starting from 4-bromobenzaldehyde and pyrrolidine by the same method (step B) described in Example 1.

Step B

The mixture of 4-bromobenzyl-pyrrolidine (1 equiv, 240 mg), Pd$_2$(dba)$_3$ (2.0% equiv, 18.3 mg), t-Bu$_3$P (1.6% equiv, 3.2 mg), benzylamine (0.5 equiv, 53.6 mg) and NaOtBu$_3$ (1.5 equiv, 144 mg) in toluene (5 mL) was heated at 70° C. for 8 h. Concentration and preparative TLC provided the title compound (80 mg). $^1$H NMR (400 MHz, CDCl$_3$) δ7.26 (m, 9 H), 7.00 (d, J=8.6 Hz, 4 H), 4.97 (s, 2 H), 3.68 (s, 4 H), 3.60 (s, 2 H), 2.68 (m, 8 H), 1.86 (m, 4 H).

Example 24

(3Piperidin-1-yl-propyl)-bis-(4pyrrolidin1-ylmethyl-phenyl)-amine K$_i$=3.5 nM The title compound was prepared starting from 4-bromobenzyl-pyrrolidine and 3-piperidin-1-yl-propyl amine by the same method (step B) described in example 23. $^1$H NMR (400 MHz, CDCl$_3$) δ7.26 (d, J=8.6 Hz, 4 H), 7.00 (d, J=8.6 Hz, 4 H), 3.74 (t, J=7.3, 2 H), 3.64 (s, 4 H), 2.60 (m, 8 H), 2.36 (m, 6 H), 1.85 (m, 10 H), 1.64 (m, 4 H), 1.46 (m, 2 H).

Example 25

(2N,N-dimethylamine)ethyl)-bis-(4pyrrolidin1-ylmethyl-phenyl)-amine

N,N-Dimethyl-N',N'-bis-(4pyrrolidin1-ylmethyl-phenyl)-athane-1,2-d K$_i$=453 nM

The title compound was prepared starting from 4-bromobenzyl-pyrrolidine and 2-(N,N-dimethylamine) ethylamine by the same method (step B) described in example 23. $^1$H NMR (400 MHz, CDCl$_3$) δ7.26 (m, 4 H), 6.96 (m, 4 H), 3.85 (t, J=7.9 Hz, 2 H), 3.60 (s, 4 H), 2.60 (m, 10 H), 2.29 (s, 6 H), 1.83 (m, 8 H).

Example 26

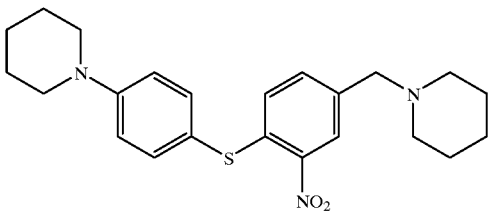

1-[4-(4-Piperidine-phenylsulfanyl)-3-nitro-benzyl]-piperidine $K_i$=756 nM

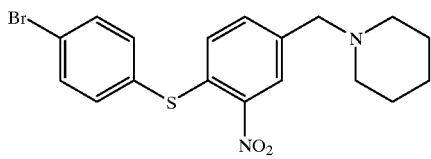

Step A 1-[4-(3-Bromo-phenylsulfanyl)-3-nitro-benzyl]-piperidine

A solution of 4-(4-Bromo-phenylsulfanyl)-3-nitro-benzaldehyde (338 mg), piperidine (98.9 μL), and acetic acid (0.12 mL) in DCM (10 mL) was treated with sodium triacetoxyborohydride (274 mg). After 5 hours, the resulting mixture was evaporated. The product was used in the next step without purification.

Step B 1-[4-(4-Piperidine-phenylsulfanyl)-3-nitro-benzyl]-piperidine

A solution of the product in step A (133 mg), sodium tert-butoxide (48 mg), tris(dibenzylideneacetone) dipalladium(0) (5.95 mg), tri-tert-butylphosphine (13 μL), and piperidine (0.33 mL) in dioxane (2 mL) was stirred at 90° C. for 16 hours. Next day, another equivalent of piperidine (0.33 mL) was added, and the reaction was stirred at 90° C. for 2 days and then concentrated. The residue was purified via preparative thin layer chromatography eluting with 1:1 DCM:EtOAc to give the title compound (35.3 mg). $^1$H NMR (400 MHz, CDCl$_3$)δ8.15 (d, J=1.8, 1 H), 7.40 (d, J=8.9, 2 H), 7.29 (dd, J=8.4, 1.9, 1 H), 6.96 (d, J=8.9, 2 H), 6.80 (d, J=8.4, 1 H), 3.42 (s, 2 H), 3.28 (m, 4 H), 2.34 (br, 4 H), 1.73 (m, 4 H), 1.62 (m, 2 H), 1.53 (m, 2 H), 1.42 (m, 2 H). $^{13}$C NMR (400 MHz, CDCl$_3$)δ152.8, 144.3, 139.6, 137.3, 136.2, 134.0, 127.8, 125.8, 117.6, 116.5, 76.7, 62.2, 54.4, 49.3, 25.9, 25.5, 24.24, 24.22.

Example 27

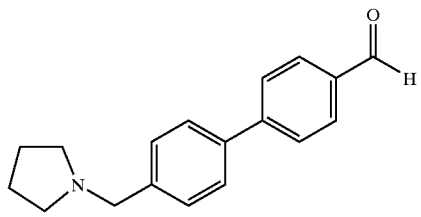

4'-Pyrrolidin-1-ylmethyl-biphenyl-4-carbaldehyde
$K_i$=8.7 nM

A solution of biphenyl-4,4'-dicarbaldehyde (0.21 g), pyrrolidine (83 μL), and acetic acid (57 μL) in DCM (5 mL) was treated with sodium triacetoxyborohyride (0.34 g). After 16 hours, the resulting mixture was treated with 3M NaOH (1.5 mL) and extracted with DCM (3×10 mL). The combined organic phases were dried over sodium sulfate and evaporated. The residue was purified via preparative thin layer chromatography eluting with 5% MeOH/DCM to give the title compound (42.5 mg). $^1$H NMR (400 MHz, CDCl$_3$) δ10.05 (s, 1 H), 7.94 (d, J=8.0, 2 H), 7.75 (d, J=8.0, 2 H), 7.60 (d, J=8.0, 2 H), 7.47 (d, J=8.0, 2 H), 3.72 (s, 2 H), 2.61 (br s, 4 H), 1.84 (br s, 4 H).

Example 28

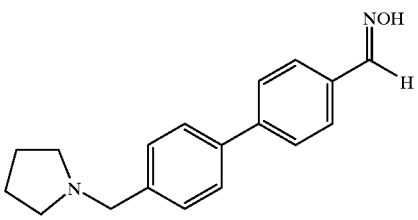

4'-Pyrrolidin-1-ylmethyl-biphenyl-4-carbaldehyde oxime
$K_i$=6.5 nM

A solution of Example 27 (33.7 mg), sodium carbonate (27.6 mg), and hydroxylamine hydrochloride (18 mg) in ethanol (5 mL) was set to reflux for 16 hours. Inorganic solid was filtered out and washed with DCM and acetone. Organic layer was concentrated under reduced pressure to give the titled compound (12 mg) without purification. $^1$H NMR (400 MHz, CDCl$_3$)δ8.19 (s, 1 H), 7.82-7.69 (m, 8 H), 4.37 (d, J=6.3, 2 H), 3.35 (m, 2 H), 3.10-3.03 (m, 2 H), 2.06-1.94 (m, 2 H), 1.93-1.88 (m, 2 H).

Example 29

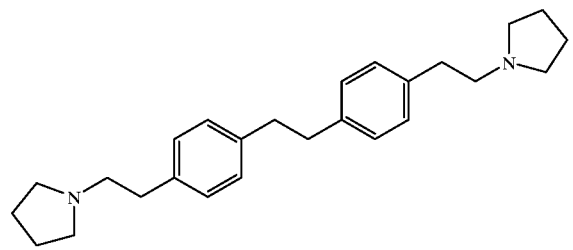

$K_i$=26.6 nM

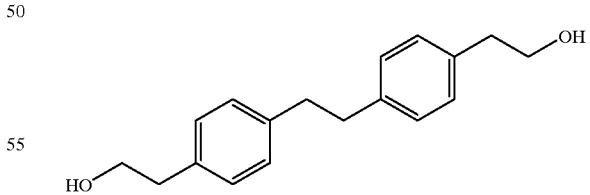

Step A 2-(4-{2-[4-(2-Hydroxy-ethyl)-phenyl]-ethyl}-phenyl)-ethanol

A solution of {4-[2-(4-ethoxycarbonylmethyl-phenyl)-ethyl]-phenyl}-acetic acid ethyl ester (0.207 g) in THF (8 mL) was protected with N$_2$ and treated with LiAlH$_4$ (0.039 g) and stirred at rt. LiAlH$_4$ was added until the reaction went to completion. It was then quenched with H$_2$O (0.1 mL), 10% NaOH (0.15 mL), and H$_2$O (0.3 mL), and filtered through celite. The filtrate was concentrated to yield the titled compound (0.101 g) and was used without further purification.

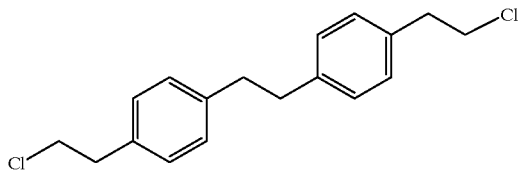

Step B 1-{2-[(2-Chloro-ethyl)-benzene]-ethyl}-4-(2-chloro-ethyl)-benzene

A solution of the product of Step A in DCM (7 mL) was treated with thionyl chloride at 30° C. for 3 days. Solvent was removed in vacuo to give the titled compound, which was used without purification.

Step C 1-(2-{4-[2-(1-Phenethyl-pyrrolidine)-ethyl]-phenyl}-ethyl)-pyrrolidine

A solution of the product of Step B in acetonitrile (10 mL) was treated with pyrrolidine (76 μL), potassium carbonate (0.174 g) and tetra-N-butylammonium iodide (5 mg). The reaction was heated at reflux until completion. Solvent was remove via vacuo and the residue was dissolved in DCM and washed with bicarbonate. The organic layer was dried over sodium sulfate, filtered and concentrated. Purification via preparative thin layer chromatography eluting with 5% MeOH/DCM to give the title compound (6.8 mg). $^1$H NMR (400, CDCI$_3$)δ7.15-7.12 (m, 8 H), 2.89-2.85 (m, 8 H), 2.79-2.66 (m, 4 H), 2.57 (m, 8 H), 1.81 (m, 8 H).

Example 30

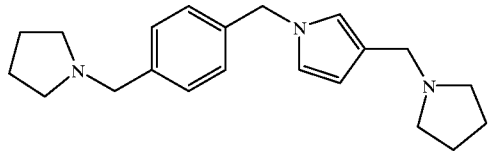

3-Pyrrolidin-1-ylmethyl-1(4pyrrolidin-1-ylmethyl-benzyl-1H-pyrrole K$_i$=24.2 nM

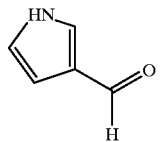

Step A Pyrrole-3-carbaldehyde

A solution of pyrrole-2-carbaldehyde (3 g) in DCE (30 mL) was treated with triflic acid and stirred at reflux for 16 hours. The reaction was cooled to rt and poured into ether (30 mL) and neutralized with potassium carbonate (47 g) and NaOH (13.6 g) in H$_2$O (20 mL). Organic layer was dried over sodium sulfate and concentrated. The residue was purified via silica gel chromatography eluting with 1:1 Ether/Hexanes to give the title compound (0.42 g).

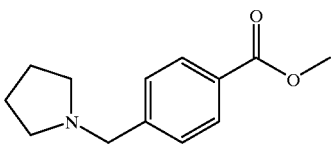

Step B 4-Pyrrolidin-1-ylmethyl-benzoic acid methyl ester

A solution of 4-formyl-benzoic acid methyl ester (10 g), pyrrolidine (5.6 mL), and acetic acid (3.5 mL) in DCM (200 mL) was treated with sodium triacetoxyborohyride (20.65 g) and stirred at rt for 16 hours. The reaction mixture was then quenched with 3N NaOH (70 mL). The organic layer was dried over sodium sulfate and concentrated to yield the titled compound without purification.

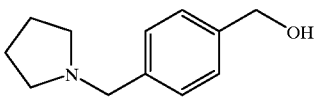

Step C (4-Pyrrolidin-1-ylmethyl-phenyl)-methanol

A solution of the product in step B (0.207 g) in THF (8 mL) was protected with N$_2$ and treated with LiAlH$_4$ (0.039 g) and stirred at rt. LiAlH$_4$ was added until the reaction went to completion. It was quenched with H$_2$O (0.1 mL), 10% NaOH (0.15 mL), and H$_2$O (0.3 mL), then filtered through celite. The filtrate was concentrated to yield the titled compound (0.101 g) and was used without further purification.

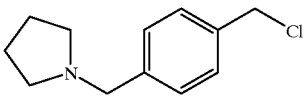

Step D 1-(4-Chloromethyl-benzyl)-pyrrolidine

A solution of the product of Step C in DCM (200 mL) was treated with thionyl chloride (20 mL) at 40° C. for 16 hours. Solvent was removed in vacuo to give the titled compound (15 g), which was used without purification.

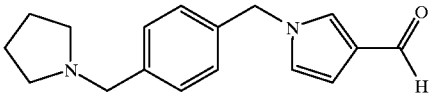

Step E 1-(4-Pyrrolidin-1-ylmethyl-benzyl)-1 H-pyrrole-3 carbaldehyde

A solution of the product in Step A (0.2 g) and Step D (0.51 g) in benzene (2 mL) was treated with 50% NaOH (2 mL), tetrabutylammonium hydrogen sulfate (84 mg) and stirred at 80° C. for 3 hours. The mixture was cooled to room temperature and diluted in water (10 mL) and extracted with ether (3×10 mL). The organic layer was dried over magnesium sulfate, filtered and concentrated to yield the titled compound (0.45 g) without purification.

Step F 3-Pyrrol id in-1-ylmethyl-1-(4-pyrrolid in-1-ylmethyl-benzyl)-1 H-pyrrole A solution of the produce from step E (0.45 g), pyrrolidine (156 μL), and acetic acid (97 μL) in DCM (6 mL) was treated with sodium triacetoxyborohyride (576 mg) and stirred at rt for 16 hours. The reaction mixture was then quenched with 3N NaOH (3 mL). The organic layer was dried over sodium sulfate and concentrated. The residue was purified via silica gel chromatography eluting with 0-5% MeOH/DCM to give the title compound (44.7 mg) as yellow oil. $^1$H NMR (400 MHz, CDCl$_3$)δ7.26 (d, J=7.9, 2 H), 7.04 (d, J=7.9, 2 H), 6.69 (s, 1 H), 6.59 (s, 1 H), 6.15 (s, 1 H), 4.98 (s, 2 H), 3.65 (s, 2 H), 3.58 (s, 2 H), 2.72 (br m, 4 H), 2.48 (br m, 4 H).

Example 31

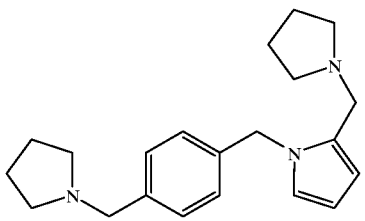

2-Pyrrolidin-1-ylmethyl-1(4pyrrolidin-1-ylmethyl-benzyl-1H-pyrrole $K_i$=3.2 nM

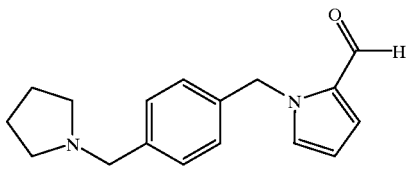

Step A 1-(4-Pyrrolidin-1-yl methyl-benzyl)-1 H-pyrrole-2-carbaldehyde

A solution of product from step D example 31 (5.2 g) and pyrrole-2-carboxaldehyde (2.0 g) in benzene (20 mL) was treated with 50% NaOH (20 mL), tetrabutylammonium hydrogen sulfate (0.8 g) and stirred at 80° C. for 3 hours. The mixture was cooled to rt and diluted in water (40 mL) and extracted with ether (3×40 mL). The organic layer was dried over magnesium sulfate, filtered and concentrated to yield the titled compound (5.2 g) without purification.

Step B 2-Pyrrolidin-1-ylmethyl-1-(4-pyrrolidin-1-ylmethyl-benzyl)-1 H-pyrrole

A solution of the produce from step A (0.46 g), pyrrolidine (156 μL), and acetic acid (97 μL) in DCM (6 mL) was treated with sodium triacetoxyborohyride (0.57 g) and stirred at rt for 16 hours. The reaction mixture was then quenched with 3N NaOH (3 mL). The organic layer was dried over sodium sulfate and concentrated. The residue was purified via silica gel chromatography eluting with 0-5% MeOH/DCM to give the title compound (0.27 g) as dark orange oil. $^1$H NMR (400 MHz, CDCl$_3$)δ7.26 (d, J=7.8, 2 H), 7.00 (d, J=7.8, 2 H), 6.62 (s, 1 H), 6.08-6.07 (m, 1 H), 6.03 (s, 1 H), 5.19 (s, 2 H), 3.57 (s, 2 H), 3.45 (s, 2 H), 2.48 (m, 4 H), 2.42 (m, 4 H), 1.77 (m, 4 H), 1.71 (m, 4 H).

Example 32

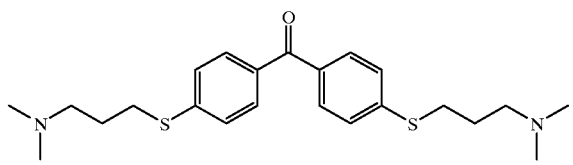

Bis-[4-(3-dimethylamino-propylsulfanyl)-phenyl] methanone dihydrochloride $K_i$=14 nM To NaH (1.59 g, 60% suspension in mineral oil) was added at room temperature n-butanol (80 mL) followed by 3-dimethylamino-propane-1-thiol hydrochloride (3.65, 85%), bis-(4-chloro-phenyl)-methanone (5.00 g), and Pd(PPh$_3$)$_4$ (4,62 g). The reaction mixture was heated under reflux for 6 h and was allowed to cool down to room temperature. Ether (500 mL) was added and the organic layer was washed with water (3×100 mL), The organic layer was extracted with HCl (1N in water, 3×150 mL) and the combined aqueous layers were washed with ether (3×200 mL) and were brought to pH=13 with NaOH (1N in water). The aqueous layers was extracted with ether (3×200 mL) and the combined organic layers were washed with water (150 mL) and brine (150 mL). The organic layers were dried over magnesium sulfate and the solvent was removed in vacuo. The crude product was separated and purified by flash chromatography on silica gel (chloroform/methanol) to give the title compound as a colorless solid (280 mg). $^1$H NMR (400 MHz, CDCl$_3$): 7.72 (d, 4 H), 7.37 (d, 4 H), 3.08 (t, 4 H), 2.43 (t, 4 H), 2.25 (s, 12 H), 1.84-1.93 (m, 4 H).

Example 33

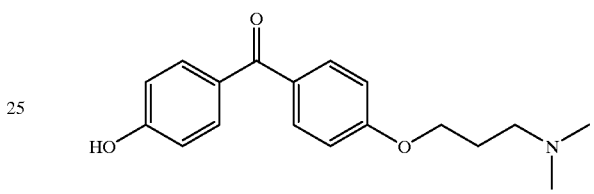

[4-(3-Dimethylamino-propoxy)-phenyl]-(4-hydroxy-phenyl)-methanone $K_i$=129nM

To a stirred solution of bis-(4-hydroxy-phenyl)-methanone (7.00 g) in methanol (130 mL) was added at room temperature t-Bu$_3$OK (14.7 g) followed by (3-chloro-propyl)-dimethyl-amine (10.3 g). The reaction mixture was heated under reflux for 18 h and was allowed to cool down to room temperature. Water (50 mL) was added and the solvent was removed in vacuo. Methylene chloride (650 mL) was added and the organic layer was washed with water (2×150 mL). The organic layer was dried over magnesium sulfate and the solvent was removed in vacuo. The crude products were separated and purified by flash chromatography on silica gel (chloroform/2 M ammonia in methanol) to give the title compound bis-[4-(3-dimethylamino-propoxy)-phenyl]-methanone as a colorless residue (250 mg). $^1$H NMR (400 MHz, CD$_3$OD): 7.78 (d, 4 H), 7.09 (d, 4 H), 4.22 (t, 4 H), 3.37-3.40 (m, 4 H), 2.96 (s, 12 H), 2.24-2.31 (m, 4 H). And title compound [4-(3-dimethylamino-propoxy)-phenyl]-(4-hydroxy-phenyl)-methanone as a colorless residue (150 mg). $^1$H NMR (400 MHz, CD$_3$OD): 7.88-7.99 (m, 4 H), 7.25-7.29 (m, 2 H), 7.08-7.13 (m, 2 h), 4.48 (t, 2 H), 2.69-2.76 (m, 2 H), 2.56 (s, 6 H), 2.23-2.30 (m, 2 H).

Example 34

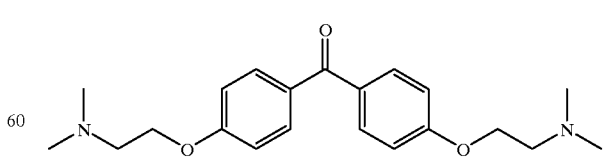

Bis-[4-(2-dimethylamino-ethoxy)-phenyl]-methanone $K_i$=126 nM

To a stirred solution of bis-(4-hydroxy-phenyl)-methanone (10.0 g) in ethanol (40.0 mL) was added at room temperature t-Bu₃OK (6.73 g) followed by (3-chloro-ethyl)-dimethyl-amine (5.76 g). The reaction mixture was heated under reflux for 24 h and was allowed to cool down to room temperature. Methylene chloride (500 mL) was added and the organic layer was washed with water (3×75 mL). The organic layer was dried over magnesium sulfate and the solvent was removed in vacuo. The crude products were separated and purified by flash chromatography on silica gel (chloroform/2 M ammonia in methanol) to give the title compound as pale brow crystals (370 mg). ¹H NMR (400 MHz, CDCl₃): 7.78 (d, 4 H), 6.98 (d, 4 H), 4.16 (t, 4 H), 2.80 (t, 4 H), 2.38 (s, 12 H).

Example 35

BIOLOGICAL METHODS

In Vitro
Transfection of Cells With Human Histamine Receptor

A 10 cm tissue culture dish with a confluent monolayer of SK-N-MC cells was split two days prior to transfection. Using sterile technique the media was removed and the cells were detached from the dish by the addition of trypsin. One fifth of the cells were then placed onto a new 10 cm dish. Cells were grown in a 37° C. incubator with 5% CO₂ in Minimal Essential Media Eagle with 10% Fetal Bovine Serum. After two days cells were approximately 80% confluent. These were removed from the dish with trypsin and pelleted in a clinical centrifuge. The pellet was then re-suspended in 400 μL complete media and transferred to an electroporation cuvette with a 0.4 cm gap between the electrodes (Bio-Rad #165-2088). One microgram of supercoiled H₃ receptor cDNA was added to the cells and mixed. The voltage for the electroporation was set at 0.25 kV; the capacitance was set at 960 μF. After electroporation the cells were diluted into 10 mL complete media and plated onto four 10 cm dishes. Because of the variability in the efficiency of electroporation, four different concentrations of cells were plated. The ratios used were; 1:20, 1:10, 1:5, with the remainder of the cells being added to the fourth dish. The cells were allowed to recover for 24 hours before adding the selection media (complete media with 600 μg/mL G418). After 10 days dishes were analyzed for surviving colonies of cells. Dishes with well isolated colonies were used. Cells from individual colonies were isolated and tested. SK-N-MC cells were used because they give efficient coupling for inhibition of adenylate cyclase. The clones that gave the most robust inhibition of adenylate cyclase in response to histamine were used for further study.

[³H]-N-methylhistamine binding

Cell pellets from histamine H₃ receptor-expressing SK-N-MC cells were homogenized in 20 mM TrisHCl/0.5 mM EDTA. Supernatants from a 800 g spin were collected, recentrifuged at 30,000 g for 30 minutes. Pellets were re-homogenized in 50 mM Tris/5 mM EDTA (pH 7.4). Membranes were incubated with 0.8 nM [³H]-N-methylhistamine plus/minus test compounds for 45 min at 25° C. and harvested by rapid filtration over GF/C glass fiber filters (pretreated with 0.3 % polyethylenimine) followed by four washes with ice cold buffer. Filters were dried, added to 4 mL scintillation cocktail and then counted on a liquid scintillation counter. Non-specific binding was defined with 10 μM histamine. The $pK_i$ values were calculated based on a $K_d$ of 800 pM and a ligand concentration ([L]) of 800 pM according to the formula:

$$K_i = (IC_{50})/(1+([L]/(K_d)))$$

In Vivo

Elucidation of oral absorption and blood-brain barrier penetration profiles of H₃ receptor antagonists in the rat A rat in vivo system was used to determine the blood-brain barrier penetration profiles and kinetics of various H₃ receptor antagonists after single bolus oral administration.

Female Sprague Dawley Rats (~300 gram body weight) were housed in accordance with institutional standards and allowed to acclimate for at least 7 days prior to the study. Each H₃ antagonist was formulated in 0.5% hydroxypropylmethyl cellulose at a concentration of 1 mg/mL for oral dosing. The test compound was administered to each of eight animals as a single oral dose of 10 mL/kg (10 mg/kg). Remaining dosing solution was retained for analysis. Two animals from each original group of eight were euthanized via CO₂ asphyxiation at t=1, 6, 24, and 48 hours. After each animal was euthanized, 0.1 mL of its blood was sampled via cardiac puncture, and its brain was removed via dissection of the cranial bones and placed in a pre-weighed 50 mL conical tube on dry ice.

The blood was added to 0.3 mL of 6% trichloroacetic acid, and the acidified sample was vortexed and then centrifuged (5 minutes at 14,000 rpm in a microcentrifuge). The clear supernatant was retained for analysis. The frozen brain was weighed, homogenized in 6% trichloroacetic acid (3 mL/g wet weight of tissue), and then centrifuged. The clear supernatant was retained for analysis. The supernatants from the blood and brain samples were analyzed by liquid chromatography with mass spectral detection utilizing selective reaction monitoring (LC-MS/MS). The LC method used a Phenomonex Polar RP column (2×50 mm) and a linear solvent gradient of water and acetonitrile (both 1% in acetic acid).

Graphs of H₃ receptor antagonist concentration versus time for blood and brain were generated from the LC-MS/MS results. The mean residency time (MRT) of the H₃ receptor antagonist, in blood or in the brain, was calculated from the ratio of the area under the first moment curve (AUMC) to the area under the concentration time curve (AUC): AUMC/AUC. The Blood Brain Barrier index was calculated from the log of $AUC_{brain}/AUC_{blood}$.

F. Other Embodiments

The features and advantages of the invention will be apparent to one of ordinary skill in view of the discussion, examples, embodiments, and claims relating to the invention. The invention also contemplates variations and adaptations, based on the disclosure herein concerning the key features and advantages of the invention, and within the abilities of one of ordinary skill.

What is claimed is:

1. A compound of formula (I):

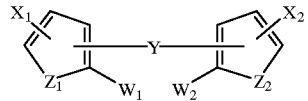

wherein each of $W_1$ and $W_2$ is H;
$X_1$ is $L_aG_a$;
$X_2$ is $L_bG_b$;
each of $G_a$ and $G_b$ is independently pyrrolidinyl, imidazolidinyl, pyrazolidinyl, piperidyl, isoindolinyl, morpholinyl, piperazinyl, imidazolyl, thiazolinyl, 5,6-dihydro-3-imidazo[2,1B]-thiazolyl, or thiazolyl;
$G_b$ can be further selected from pyrrolyl;
each of $L_a$ and $L_b$ is independently $C_{1-3}$ alkylene;

Y is a covalent bond;

$Z_1$ is —CH=CH— to form a phenyl ring and $Z_2$ is O or S;

or a pharmaceutically acceptable salt, amide or ester thereof.

2. A compound of claim 1, wherein each of $G_a$ and $G_b$ is independently pyrrolidinyl, imidazolidinyl, pyrazolidinyl, piperidyl, isoindolinyl, morpholinyl, piperazinyl, imidazolyl, thiazolinyl, 5,6-dihydro-3-imidazo[2,1-B]thiazolyl, or thiazolyl.

3. A compound of claim 1, wherein $X_1$ and $X_2$ are independently selected from pyrrolidinylmethyl, and piperidylmethyl.

4. A compound of claim 1 wherein $X_1$ and $X_2$ are the same.

5. A compound of claim 1, wherein each of $G_a$ and $G_b$ is independently pyrrolidinyl, imidazolidinyl, pyrazolidinyl, piperidyl, isoindolinyl, morpholinyl, thiazolyl, thiazolinyl, 5,6-dihydro-3-imidazo[2,1-thiazolyl, or piperazinyl.

6. A compound of claim 1, selected from the group consisting of:

1-[(4-(4-Pyrrolidin-1-ylmethyl-phenyl)-thiophen)-2-ylmethyl]-pyrrolidine;

1-[(4-(4-Pyrrolidin-1-ylmethyl-phenyl)-furan)-2-ylmethyl]-pyrrolidine;

1-((4-(4-Pyrrolidin-1-ylmethyl-thiophen)-2-ylthiophen)-2-ylmethyl)-pyrrolidine;

1-[(2-(4-Pyrrolidin-1-ylmethyl-phenyl)-thiophen)-3-ylmethyl]-pyrrolidine; and

1-[(3-(4-Pyrrolidin-1-ylmethyl-phenyl)-thiophen)-2-ylmethyl]-pyrrolidine.

7. A pharmaceutical composition, comprising a compound of claim 1 and a pharmaceutically acceptable carrier.

* * * * *